US006310195B1

(12) United States Patent
Colucci et al.

(10) Patent No.: US 6,310,195 B1
(45) Date of Patent: *Oct. 30, 2001

(54) NUCLEIC ACID ENCODING A LECTIN-DERIVED PROGENITOR CELL PRESERVATION FACTOR

(75) Inventors: M. Gabriella Colucci, Dugenta (IT); Maarten J. Chrispeels, La Jolla, CA (US); Jeffrey G. Moore, New York, NY (US)

(73) Assignee: ImClone Systems Incorporated, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/881,189

(22) Filed: Jun. 24, 1997

(51) Int. Cl.$^7$ ............................ C07H 21/04; C12N 5/16
(52) U.S. Cl. ......................... 536/23.6; 435/375; 435/377
(58) Field of Search .......................... 536/23.6; 435/375, 435/377

(56) References Cited

U.S. PATENT DOCUMENTS

| | | | |
|---|---|---|---|
| 4,808,611 | 2/1989 | Cosman | 514/12 |
| 5,186,931 | 2/1993 | Kishimoto et al. | 424/85.2 |
| 5,472,867 | 12/1995 | Kanz et al. | 435/240.25 |
| 6,084,060 | * 4/2000 | Moore | 530/200 |

FOREIGN PATENT DOCUMENTS

WO 95/00554    1/1995  (WO).

OTHER PUBLICATIONS

Van Damme, E.J.M., et al., A lectin and a lectin–related protein are the two most prominant proteins in the bark of yellow wood (*Clastrastis lutea*). Plant Mol. Biol. 29(3):579–598, Mar. 1995.*

Kuby, J. *Immunology*, W. H. Freeman & Co., NY, p. 95, 1992.*

Altabella T and Chrispeels MJ, "Tobacco Plants Transformed with the Bean βai Gene Express an Inhibitor of Insect β–Amylase in Their Seeds", *Plant Physiol.* 93:805–810 (1990).

An G, Ebert PR, Mitra A and Ha SB, "Binary Vectors", *Plant Molecular Biology Manual* A3:1–19 (1988).

Barondes SH, "Bifunctional Properties of Lectins: Lectins Redefined", *Trends in Biochemical Sciences* 13:480–482 (1988).

Berardi AC, Wang A, Levine JD, Lopez P and Scadden DT, "Functional Isolation and Characterization of Human Hematopoietic Stem Cells", *Science* 267:104–108 (1995).

Borge OJ, Ramsfjell V, Veiby OP, Murphy Jr. MJ, Lok S and Jacobsen SEW, "Thrombopoietin, But Not Erythropoietin Promotes Viability and Inhibits Apoptosis of Multipotent Murine Hematopoietic Progenitor Cells In Vitro", *Blood* 88(8):2859–2870 (1996).

Dexter and Spooncer, "The Structure of the Hemopoietic System", *Cell Biol.* 3:423–441 (1987).

Dosil M, Wang S and Lemischka IR, "Mitogenic Signalling and Substrate Specificity of the Flk2/Flt3 Receptor Tyrosine Kinase in Fibroblasts and Interleukin 3–Dependent Hematopoietic Cells", *Molecular and Cellular Biology* 13(10):6572–6585 (1993).

Dwek RA, "Glycobiology: More Functions for Oligosaccharides", *Science* 269:1234–1235 (1995).

Gabius H–J, "Non–Carbohydrate Binding Partners/Domains of Animal Lectins", *Int. J. Biochem.* 26(4):469–477 (1994).

Gowda LR, Savithri HS and Rao R, "The Complete Primary Structure of a Unique Mannose/Glucose–Specific Lectin from Field Bean (*Dolichos lab lab*)", *The Journal of Biological Chemistry* 269(29):18789–18793 (1994).

Hao Q–L, Thiemann FT, Petersen D, Smogorzewska EM and Crooks GM, "Extended Long–Term Culture Reveals a Highly Quiescent and Primitive Human Hematopoietic Progenitor Population", *Blood* 88(9):3306–3313 (1996).

Higgins TJV, Newbigin EJ, Spencer D, Llewellyn DJ and Craig S, "The Sequence of a Pea Vicilin Gene and its Expression in Transgenic Tobacco Plants", *Plants Molecular Biology* 11:683–695 (1988).

Hoffman LM, Ma Y, Barker RF, "Molecular Cloning of *Phaseolus Vulgaris* Lectin mRNA and Use of cDNA as a Probe to Estimate Lectin Transcript Levels in Various Tissues" *Nucleic Acids Research* 10(23):7820–7829 (1982).

Kuriyama M, Harada N, Kuroda S, Yamamoto T, Nakafuku M, Iwamatsu A, Yamamoto D, Prasad R, Croce C, Canaani E and Kaibuchi, K, "Identification of AF–6 and Canoe as Putative Targets for Ras*", *The Journal of Biological Chemistry* 271(2):607–610 (1996).

(List continued on next page.)

*Primary Examiner*—David Saunders
*Assistant Examiner*—Mary Beth Tung
(74) *Attorney, Agent, or Firm*—Hale and Dorr LLP

(57) ABSTRACT

The invention relates to an isolated nucleic acid molecule that encodes a protein that is effective to preserve progenitor cells, such as hematopoietic progenitor cells. The nucleic acid comprises a sequence defined by SEQ ID NO:1, a homolog thereof, or a fragment thereof. The encoded protein has an amino acid sequence that comprises a sequence defined by SEQ ID NO:2, a homolog thereof, or a fragment thereof that contains an amino acid sequence TNNVLQVT. Methods of using the encoded protein for preserving progenitor cells in vitro, ex vivo, and in vivo are also described. The invention, therefore, include methods such as myeloablation therapies for cancer treatment wherein myeloid reconstitution is facilitated by means of the specified protein. Other therapeutic utilities are also enabled through the invention, for example, expanding progenitor cell populations ex vivo to increase chances of engraftation, improving conditions for transporting and storing progenitor cells, and facilitating gene therapy to treat and cure a broad range of life-threatening hematologic diseases.

17 Claims, 14 Drawing Sheets

OTHER PUBLICATIONS

Marfatia SM, Lue RA, Branton D and Chishti AH, "Identification of the Protein 4.1 Binding Interface on Glycophorin C and p55, a Hmologue of the Drosophila discs–large Tumor Suppressor Protein*", *The Journal of Biological Chemistry* 270(2):715–719 (1995).

Moreno J and Chrispeels MJ, "A Lectin Gene Encodes the β–amylase Inhibitor of the Common Bean", *Proc. Natl. Acad. Sci. USA* 86:7885–7889 (1989).

Mosmann T, "Rapid Colorimetric Assay for Cellular Growth and Survival: Application to Proliferation and Cytotoxicity Assays", *Journal of Immunological Methods* 65:55–63 (1983).

Opdenakker C, Rudd PM, Wormald M, Dwek RA and Van Damme J, "Cells Regulate the Activities of Cytokines by Glycosylation", *The FASEB Journal* 9:453–457 (1995).

Pueyo JJ, Chrispeels MJ and Herman EM, "Degradation of Transport–Competent Destabilized Phaseolin with a Signal for Retention in the Endoplasmic Reticulum Occurs in the Vacuole", *Planta* 196:586–596 (1995).

Shah AJ, Smogorzewska EM, Hannum C and Crooks GM, "Flt3 Ligand Induces Proliferation of Quiescent Human Bone Marrow CD34+CD38− Cells and Maintains Progenitor Cells In Vitro", *Blood* 87(9):3563–3570 (1996).

Sharon N and Lis H, "Lectins as Cell Recognition Molecules", *Science* 246:227–234 (1989).

Small D, Levenstein M, Kim E, Carow C, Amin S, Rockwell P, Witte L, Burrow C, Ratajczak MZ, Gewirtz AM and Civin CI, "STK–1, the Human Hmolog of Flk–2/Flt–3, is Selectively Expressed in CD34+Human Bone Marrow Cells and is Involved in the Proliferation of Early Progenitor/Stem Cells", *Proc. Natl. Acad. Sci. USA* 91:459–463 (1994).

Tessler S, Rockwell P, Hicklin D, Cohen T, Levi B–Z, Witte L, Lemischka IR, Neufeld G, "Heparin Modulates the Interaction of $VEGF_{165}$ with Soluble and Cell Associated flk–1 Receptors", *The Journal of Biological Chemistry* 269(17):12456–12461 (1994).

Turhan AG, Humphries K, Phillips GL, Eaves AC and Eaves CJ, "Clonal Hematopoiesis Demonstrated by X–Linked DNA Polymorphisms After Allogeneic Bone Marrow Transplantation", *The New England Journal of Medicine* 320(25):1655–1661 (1989).

Young JC, Varma A, DiGiusto D and Backer MP, "Retention of Quiescent Hematopoietic Cells with High Proliferative Potential During Ex Vivo Stem Cell Culture", *Blood* 87(2):545–556 (1996).

Zipori D, "Regulation of Hemopoiesis by Cytokines that Restrict Options for Growth and Differentiation", *Cancer Cells* 2(7):205–211 (1990).

Zipori D, "The Renewal and Differentiation of Hemopoietic Stem Cells", *The FASEB Journal* 6:2691–2697.

* cited by examiner

β-Subunit

```
Gowda    1  AQSLSFSFTKFDPNQEDLIFQGTATS..........KLDSAGNPVSSSAGRV   42
            ||||||||||||||||||||||||||          ||||||||||||||||
FRIL     1  AQSLSFSFTKFDPNQEDLIFQGHATSTNNVLQVTKLDSAGNPVSSSAGRV   50

Gowda   43  LYSAPLRLRLWEDSAVLTSFDPTIY...IFTNYTSRIADGLA.FIAPPDSVIS  89
            ||||||||||||||||||||| ||   ||.|||||||||| | |||||||||
FRIL    51  LYSAPLRLRLWEDSAVLTSFDTIINFEISTPYTSRIADGLAFFIAPPDSVIS 100

Gowda   90  YHGGFLGLFPNAAESG.......  105
            ||||||||||||. ..
FRIL   101  YHGGFLGLFPNANTLNNSSTSEN  123
```

α-Subunit

```
Gowda    1  ......IAESNVVAVEFDTDYLNPDYGDPNYIHIGIDVNSIRSKVTASWDW   45
                  |.||:|||||||| ||||||||||||||||||||||||||.||
FRIL     1  QTTTKAASSNVVAVEFDT.YLNPDYGDPNYIHIGIDVNSIRSKVTAKWDW   49

Gowda   46  QNGKIATAHISYNSVSKRLSVTTYYPGRGKPATSYDIELHTVLPEWVRVG   95
            |||||||||||||||||||||||.|:.|:..||||||||||||||||||
FRIL    50  QNGKIATAHISYNSVSKRLSVTSYYAGSKPATLSYDIELHTVLPEWVRVG   99

Gowda   96  LSASTGQNIERNTVHSWSFTSSLWTNVAKVGVASISG............  132
            ||||||:::|||||||||||||||||||:.: 
FRIL   100  LSASTGQDKERNTVHSWSFTSSLWTNVAKKENENKYITRGVL**YMCIND  149
```

FIG. 2

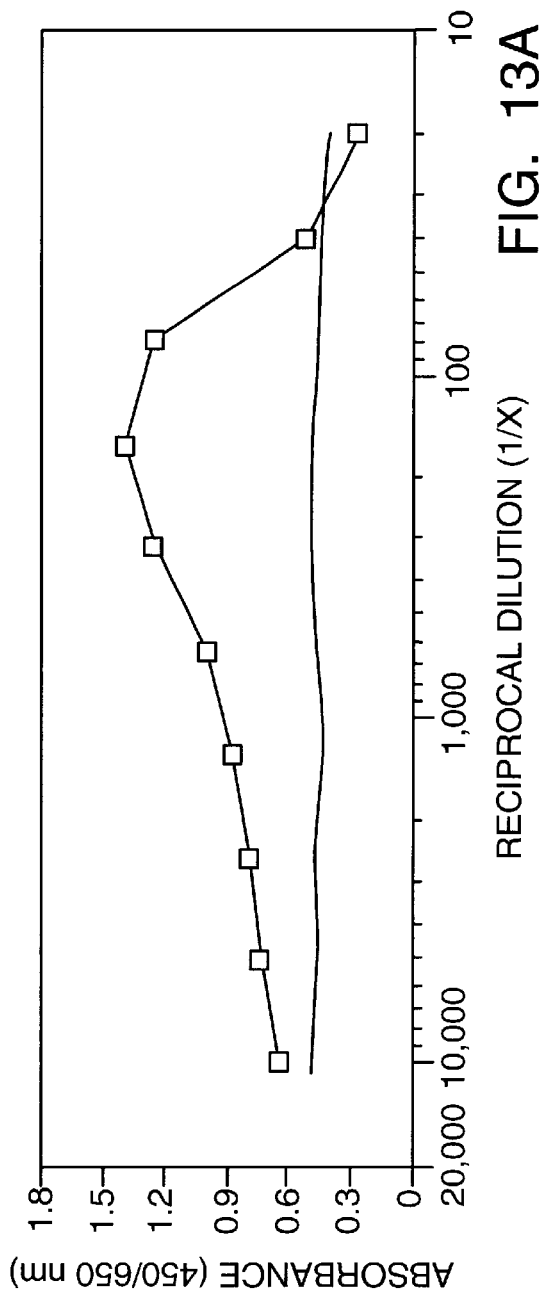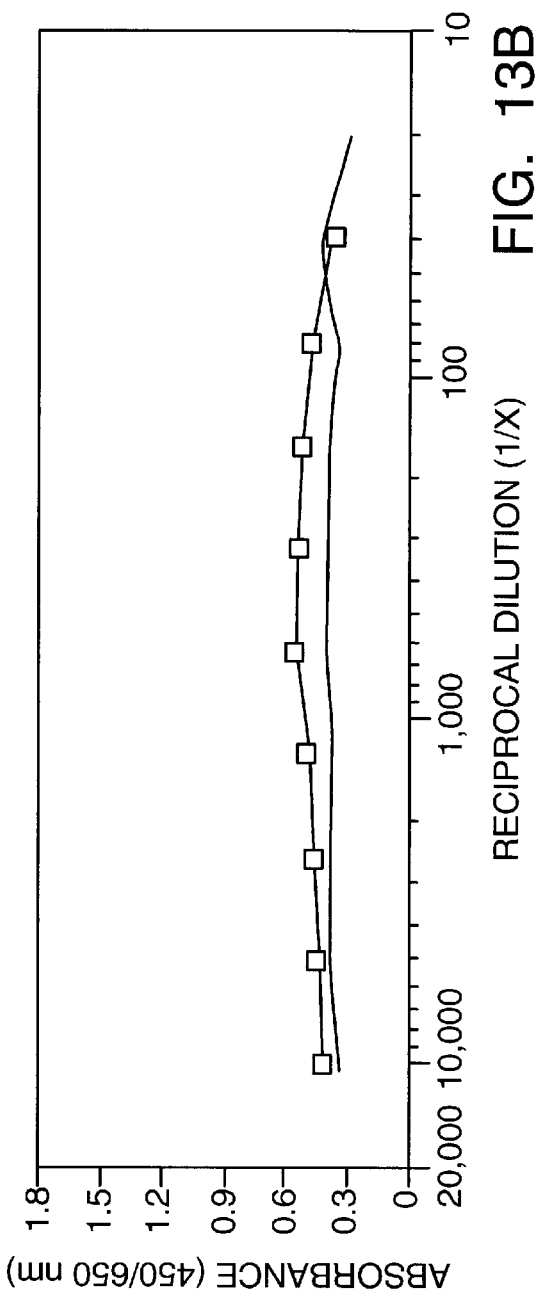

NUCLEIC ACID ENCODING A LECTIN-DERIVED PROGENITOR CELL PRESERVATION FACTOR

BACKGROUND OF THE INVENTION

The invention relates to a nucleic acid and its corresponding protein for use in connection with the preservation of progenitor cells. More specifically, the invention relates to a nucleic acid and the protein that it encodes and which is capable of preserving progenitor cells, as well as a method of using the protein for preserving progenitor cells.

Each day the bone marrow generates and releases into the circulation several billion fully-differentiated, functional blood cells. Production of these cells derives from a small stock of quiescent progenitor cells (including the most primitive stem cells and other less primitive but still immature progenitors) by a process called hematopoiesis (Zipori 1992). The most primitive stem cells have the capacity to generate >$10^{13}$ cells containing all blood lineages (Turhan et al. 1989). The production of such a large number of cells is achieved by extensive proliferation coupled with successive differentiation steps leading to a balanced production of mature cells. Progenitor cells progressively lose their capacity to generate multiple cells lineages and eventually produce cells of one or two cell lineages.

Soluble regulators and cell-cell interactions mediate differentiation pathways of immature progenitors through a tightly-controlled but inadequately understood process. Several of the body's soluble factors have been isolated and characterized both in culture and in animals (see, e.g., Ogawa (1993) and references therein). Regulators such as the colony stimulating factors (e.g., IL3, GM-CSF, G-CSF, M-CSF) not only induce proliferation and differentiation of progenitors capable of producing cells of either multiple cell lineages (IL3 and GM-CSF) or single cell lineages (G-CSF and M-CSF), but also preserve viability of their respective progenitors for short periods. Other regulators such as interleukin-1 (IL1), the kit ligand (KL), and thrombopoietin (Borge et al. 1996) increase viability of multipotential progenitors in addition to other functions. No known cytokines alone or in combination can preserve viability of primitive progenitors in liquid culture without stromal support beyond a few days.

Regulation of primitive stem cells appears to differ from that of immature, multilineage progenitors. Hematopoietic stem cells, which reside in the bone marrow predominantly in a quiescent state, do not appear to respond immediately to regulators that induce differentiation and proliferation. Maintenance of these cells in the body is mediated via cell-cell interactions and soluble regulators. Maintenance of quiescent stem cells in vitro has been achieved by culturing cells on adherent stromal layers with soluble regulators such as IL3, IL6, KL and LIF (Young et al. 1996). Recently, the addition of the FLK2/FLT3 ligand (FL) to this complex culture has been found to extend maintenance of quiescent stem cells from a few weeks to three months (Shah et al. 1996).

While the use of stromal cell culture has heretofore proven to be useful for the maintenance of hematopoietic stems cells in the laboratory setting, such approaches are not easily amenable to clinical application. Isolating and establishing stromal cell cultures for individual patients is not practical either because of time constraints or because a patient's marrow may be compromised by the underlying disease or exposure to agents (e.g., radiation, chemotherapy) that can damage the bone marrow microenvironment.

Lectins, defined as carbohydrate-binding proteins other than antibodies or enzymes, (Baronedes 1988), are widespread among plants, prokaryotes, and eukaryotes (see generally, Gabius et al. 1993). Each lectin recognizes a specific carbohydrate moiety, and forms a non-covalent bond with the carbohydrate through a stereochemical fit of complementary domains (e.g., hydrophobic pocket). Carbohydrates are widely present on cell surfaces (in the forms of glycoproteins, glycolipids, and polysaccharides), and appear to mediate cell—cell contacts including cell recognition (Sharon et al. 1989). Abnormal glycosylation patterns are associated with disease by causing alterations in a protein's surface properties, conformation, stability, or protease resistance (Dwek 1995).

Gowda et al. (1994) described the isolation of a mannose-glucose-specific lectin from the hyacinth bean (*Dolichos lab lab*). Purification and sequencing of this lectin is said to indicate that the protein includes two nonidentical subunits. The Gowda et al. publication describes evolutionary relationships of the lectin to other lectins, but does not ascribe any function to the protein beyond saccharide-binding.

Cell agglutinating properties of certain plant lectins have been known for over 100 years. Certain lectins have been used as tools in immunology laboratories as potent, specific activators of T lymphocytes (phytohemagglutinin (PHA) and concanavalin A (ConA)) and B lymphocytes (pokeweed mitogen (PWM)) for over 30 years (Sharon et al. 1989). Some lectins have also been used to isolate hematopoietic progenitors for over 15 years (Gabius 1994a). Large numbers of cancer patients in Europe have received crude extracts of mistletoe lectin (*Viscum album*) intravenously as a candidate cancer therapy without major complications (Gabius 1994b). Whether these plant lectins act on mammalian cells via de novo means, or simply mimic their functional mammalian homologs is not yet known. No lectin has yet been successfully developed as a human therapeutic.

In view of the above considerations, it is clear that regulation of the hematopoietic process remains incompletely understood. Most soluble regulators identified, such as the colony stimulating factors and interleukins, induce proliferation and differentiation of progenitors cells in culture and their levels in the blood circulation increase during times of hematopoietic stress (e.g., blood loss, infection). For example, U.S. Pat. No. 4,808,611 describes a method of using IL1 and a colony stimulating factor to induce proliferation and differentiation of hemopoietic stem cells. Some soluble regulators, such as IL1, IL6, IL11, KL, FL, and Tpo, marginally increase viability of primitive progenitors on their own, but when added in combination induce proliferation and differentiation of progenitors. Soluble regulators that maintain or expand primitive progenitors for extended periods in the absence of stromal support are not yet commercially available. As a consequence, numerous potential therapeutic approaches to diseases such as cancer and genetic blood diseases remain unexplored.

Accordingly, it is one of the purposes of this invention to overcome the above limitations in methods of regulating hematopoietic processes, by providing a factor and method of protecting, preserving, and expanding hematopoietic progenitor cell populations. It is another purpose of the invention to provide means for protecting the integrity of the hematopoietic processes in vivo as an adjunct to therapeutic treatments related to cancer and other diseases that can otherwise adversely impact upon the hematopoietic system.

SUMMARY OF THE INVENTION

It has now been discovered that these and other objectives can be achieved by the present invention, which provides an isolated nucleic acid comprising a nucleotide sequence as defined by SEQ ID NO:1, a homolog thereof, or a unique fragment thereof that encodes an amino acid sequence TNNVLQVT (SEQ ID NO.:24).

The isolated nucleic acid preferably encodes a mannose/glucose-specific legume lectin, and is more preferably isolated from a legume of the tribe Phaseoleae. Most preferably, the protein is encoded by a nucleic acid that is isolated from red kidney beans, white kidney beans, hyacinth beans, or black-eyed peas. The isolated nucleic acid of the invention preferably comprises a nucleotide sequence as defined by SEQ ID NO:1 or a unique fragment thereof.

Also, the protein encoded by the nucleic acid of the invention is capable of preserving progenitor cells that are at least unipotent progenitor cells, but the protein can be used to preserve pluripotent progenitor cells, as well as totipotent progenitor cells. In a preferred case, the protein can preserve hematopoietic progenitor cells, but progenitor cells from other tissues can also be preserved, including nerve, muscle, skin, gut, bone, kidney, liver, pancreas, or thymus progenitor cells. The progenitor cells capable of preservation according to the invention may express the CD34 antigen. More preferably, the progenitor cells express both CD34 and the FLK2/FLT3 receptor. Still more preferably, the progenitor cells express the FLK2/FLT3 receptor but do not express CD34. The protein can also be used to preserve cells that have been modified to express FLK2/FLT3 receptors on their surface. Thus, the invention provides a protein that has significant binding affinity for FLK2/FLT3 receptor on the cells, wherein binding of the protein with the FLK2/FLT3 receptor mediates the inhibition of differentiation of the cells.

The invention further provides a method for preserving progenitor cells, comprising contacting progenitor cells with a protein encoded by an isolated nucleic acid comprising a nucleotide sequence defined by SEQ ID NO:1, a homolog thereof, or a fragment thereof that encodes an amino acid sequence TNNVLQVT, in an amount sufficient to preserve the progenitor cells.

The method of the invention is useful for preserving progenitor cells from other species, particularly mammalian species. The progenitor cells preferably comprise cells of hematopoietic origin. The method can be used for preserving any human progenitor cells that express the CD34 antigen and/or the FLK2/FLT3 receptor. Alternatively, the method can be used to preserve any murine progenitor cells that express the Sca antigen, but that do not express mature blood cell lineage antigens.

The method can comprise contacting the progenitor cells with the protein in vitro, ex vivo, or in vivo. In addition, the method can further comprise contacting the progenitor cells with FLK2/FLT3 ligand in an amount sufficient to selectively expand the number of progenitor cells without inducing differentiation thereof In another embodiment, the invention is a method of treating a mammal in need of hematopoietic therapy, comprising:
a) obtaining a tissue sample from the mammal, the tissue sample comprising hematopoietic progenitor cells;
b) culturing the progenitor cells in the presence of a protein that preserves the progenitor cells, to provide cultured cells enriched in the progenitor cells, wherein the protein is encoded by an isolated nucleic acid comprising a nucleotide sequence defined by SEQ ID NO:1, a homolog thereof, or a fragment thereof that encodes an amino acid sequence TNNVLQVT;
c) subjecting the mammal to conditions sufficient to effect myeloablation; and
d) administering the cultured cells to the mammal following the myeloablation to reconstitute the hematopoietic system of the mammal.

According to the method, the myeloablation conditions can comprise bone marrow irradiation, whole body irradiation, or chemically-induced myeloablation.

In another embodiment, the invention is a method of enriching progenitor cells, comprising culturing progenitor cells in a progenitor-preserving amount of a protein encoded by an isolated nucleic acid comprising a nucleotide sequence defined by SEQ ID NO:1, a homolog thereof, or a fragment thereof that encodes an amino acid sequence TNNVLQVT, wherein the protein specifically preserves the progenitor cells, and wherein the culturing is performed under conditions permitting preservation of progenitor cells while permitting the number of differentiated cells to decrease.

The method can be used to enrich progenitor cells, such as primitive progenitor cells, as well as mature progenitor cells. Preferably, the progenitor cells are at least substantially free of stromal cells.

The culturing conditions used in the method can include culturing in a medium containing a cytotoxic agent that exhibits selective toxicity for proliferating cells. Suitable cytotoxic agents include, for example, adriamycin, cyclophosphamide, taxol or other taxane, cisplatin, or 5-fluorouracil.

In still another embodiment, the invention is a method of improving hematopoietic competence in a mammal, comprising:
a) culturing a tissue sample comprising hematopoietic progenitor cells in a growth medium containing a protein encoded by an isolated nucleic acid comprising a nucleotide sequence defined by SEQ ID NO:1, a homolog thereof, or a fragment thereof that encodes an amino acid sequence TNNVLQVT, in an amount sufficient to preserve the progenitor cells and to provide cultured cells enriched in the progenitor cells; and
b) transfusing the enriched cultured cells to the mammal to provide progenitor cells for generating blood cellular components in the mammal.

According to the method, the tissue sample can comprise peripheral blood, umbilical cord blood, placental blood, or bone marrow. Preferably, the tissue sample is autologous to the mammal. It is also preferred that the tissue sample is at least substantially free of stromal cells. The method can further comprise ablating hematopoietic tissues in the mammal prior to the transfusing.

In yet a further embodiment, the invention is an improvement to a method of transfecting an exogenous DNA sequence into somatic cells, in which the improvement comprises transfecting progenitor cells selectively preserved by a protein encoded by an isolated nucleic acid comprising a nucleotide sequence defined by SEQ ID NO:1, a homolog thereof, or a fragment thereof that encodes an amino acid sequence TNNVLQVT.

In another embodiment, the invention is a composition for preserving viability of progenitor cells ex vivo, comprising a cell growth medium and a protein that preserves progenitor cells, wherein the protein is encoded by an isolated nucleic acid comprising a nucleotide sequence defined by SEQ ID NO:1, a homolog thereof, or a fragment thereof that encodes an amino acid sequence TNNVLQVT.

In a still further embodiment, the invention is a method for preserving progenitor cells in a mammal, comprising:
a) administering to the mammal a protein that specifically preserves progenitor cells, the protein being encoded by an isolated nucleic acid comprising a nucleotide sequence defined by SEQ ID NO:1, a homolog thereof, or a fragment thereof that encodes an amino acid sequence TNNVLQVT, in an amount sufficient to preserve progenitor cells of the mammal in a substantially non-proliferative state;

b) exposing the mammal to myeloablative conditions sufficient to effect ablation of proliferating myeloid cells but sparing non-proliferating progenitor cells; and c) following the exposing, reestablishing proliferation or differentiation of the preserved progenitor cells.

According to the method, the reestablishing can comprise administering to the mammal a cytokine in an amount sufficient to improve the viability of the progenitor cells. The viability-improving cytokine can be IL-1, IL-3, IL-6, IL-11, KL, or a combination thereof. The method can be further modified such that the reestablishing comprises administering to the mammal a proliferation-stimulating amount of the FLK2/FLT3 ligand.

These and other advantages of the present invention will be appreciated from the detailed description and examples that are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein:

FIG. 2 is a direct amino acid sequence comparison of the mannose lectin described by Gowda et al. (1994) and the derived amino acid sequence of the protein encoded by the nucleic acid of the invention.

FIG. 13A is a graph showing that a crude extract of an E. coli culture containing expressed FRIL specifically stimulates hFLK2/FLT3 3T3 cells; FIG. 13B is a graph showing that the same extract does not stimulate untransfected 3T3 cells.

DETAILED DESCRIPTION OF THE PREFERRED EMBODIMENTS

Figure 1:
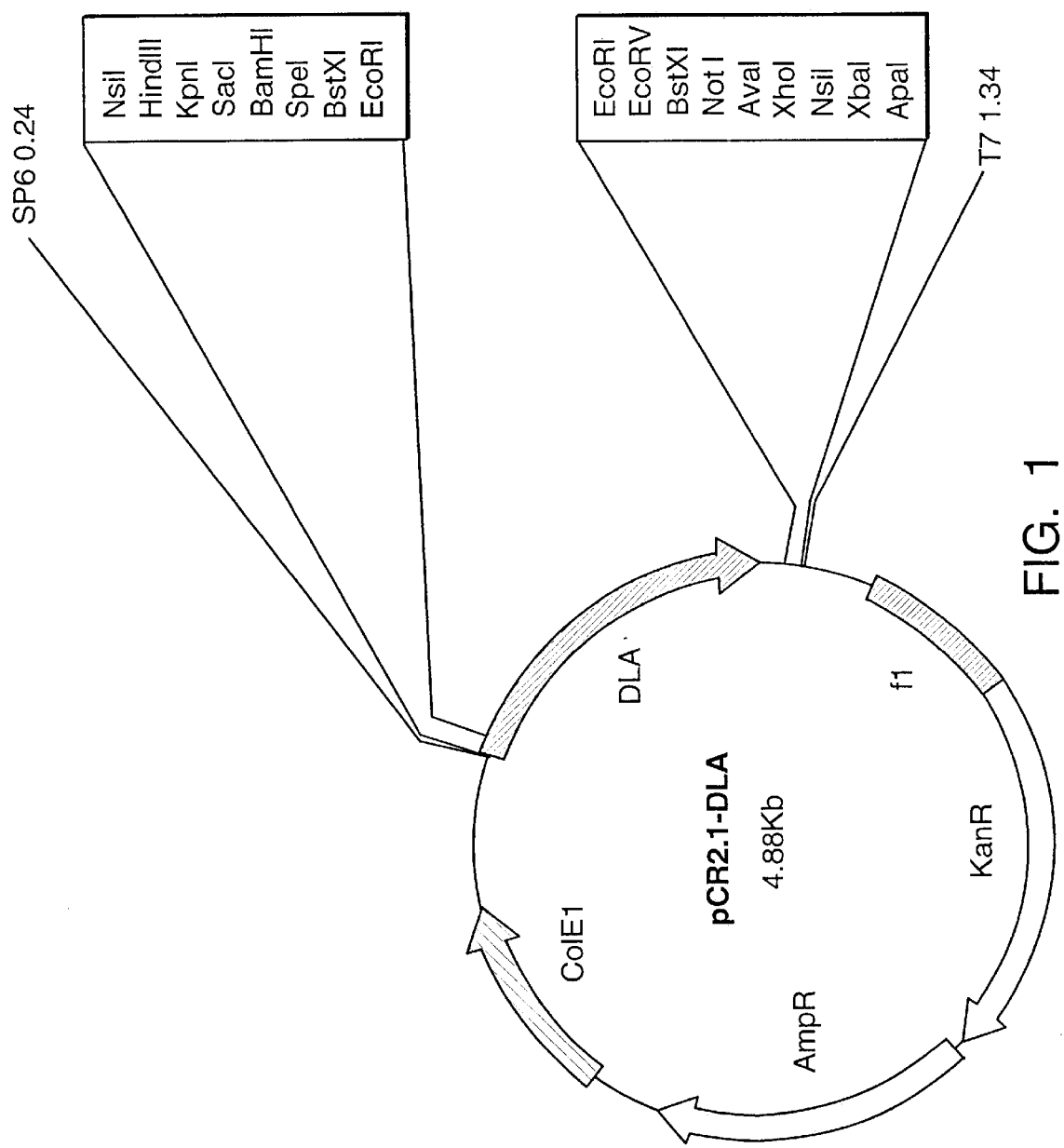
FIG. 1 is a map of a cloning vector pCR2.1-DLA manufactured by ligating a cDNA according to the invention in the EcoRI site of the cloning vector pCR2.1.

The present invention is directed to an isolated nucleic acid encoding a protein that preserves progenitor cells, and, therefore, the invention further includes a method of using the nucleic acid in producing the encoded protein, and a method of using the encoded protein in preserving progenitor cells.

Applicants have isolated and sequenced a nucleic acid having the sequence defined by SEQ ID NO:1, and homologs thereof, including homologs in other species. The invention further comprises unique fragments of the nucleic acid of SEQ ID NO:1 and its homologs.

The protein encoded by the nucleic acid sequence defined by SEQ ID NO:1 has the amino acid sequence defined by SEQ ID NO:2. But the invention also encompasses isolated nucleic acid molecules that encode unique portions of the protein specified as SEQ ID NO:2. Specifically, the invention includes nucleic acids that encode proteins that contain the sequence TNNVLQVT (SEQ ID NO.:24), which is a part of SEQ ID NO:2, as well as functional equivalents thereof.

"Nucleic acid," as used herein, means any deoxyribonucleic acid (DNA) or ribonucleic acid (RNA) that encodes in its nucleotide sequence a protein as described herein or a unique fragment thereof. The fragment can be an oligonucleotide (i.e., about 8 to about 50 nucleotides in length) or a polynucleotide (about 50 to about 2,000 or more nucleotides in length). For example, nucleic acids include messenger RNA (mRNA), complementary DNA (cDNA), genomic DNA, synthetic DNA or RNA, and the like. The nucleic acid can be single stranded, or partially or completely double stranded (duplex). Duplex nucleic acids can be homoduplex or heteroduplex.

The invention specifically includes nucleic acids that have a nucleotide sequence including the sequence defined by SEQ ID NO:1, or a homolog thereof, or unique fragments thereof In the present specification, the sequence of a nucleic acid molecule that encodes the protein is considered homologous to a second nucleic acid molecule if the nucleotide sequence of the first nucleic acid molecule is at least about 30% homologous, preferably at least about 50% homologous, and more preferably at least about 65% homologous to the sequence of the second nucleic acid molecule. In the case of nucleic acids having high homology, the nucleotide sequence of the first nucleic acid molecule is at least about 75% homologous, preferably at least about 85% homologous, and more preferably at least about 95% homologous to the nucleotide sequence of the second nucleic acid molecule. For example, a test for homology of two nucleic acid sequences is whether they hybridize under normal hybridization conditions, preferably under stringent hybridization conditions.

Given the nucleic acid sequence disclosed herein, the artisan can further design nucleic acid structures having particular functions in various types of applications. For example, the artisan can construct oligonucleotides or polynucleotides for use as primers in nucleic acid amplification procedures, such as the polymerase chain reaction (PCR), ligase chain reaction (LCR), Repair Chain Reaction (RCR), PCR oligonucleotide ligation assay (PCR-OLA), and the like. Oligonucleotides useful as probes in hybridization studies, such as in situ hybridization, can be constructed. Numerous methods for labeling such probes with radioisotopes, fluorescent tags, enzymes, binding moieties (e.g., biotin), and the like are known, so that the probes of the invention can be adapted for easy detectability.

Oligonucleotides can also be designed and manufactured for other purposes. For example, the invention enables the artisan to design antisense oligonucleotides, and triplex-forming oligonucleotides, and the like, for use in the study of structure/function relationships. Homologous recombination can be implemented by adaptation of the nucleic acid of the invention for use as targeting means.

As a new and specific nucleotide sequence is disclosed herein, the artisan will recognize that the nucleic acid can be produced by any synthetic or recombinant process such as is well known in the art. Nucleic acids according to the invention can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences. Methods for modifying nucleic acids to achieve specific purposes are disclosed in the art, for example, in Sambrook et al. (1989) and, the disclosure of which is incorporated by reference herein. Moreover, the nucleic acid can include one or more portions of nucleotide sequence that are non-coding for the protein of interest.

The skilled artisan appreciates that, if an amino acid sequence (primary structure) is known, a family of nucleic acids can then be constructed, each having a sequence that differs from the others by at least one nucleotide, but where each different nucleic acid still encodes the same protein. For example, if a protein has been sequenced but its corresponding gene has not been identified, the gene can be acquired through amplification of genomic DNA using a set of degenerate primers that specify all possible sequences encoding the protein.

The protein encoded by the nucleic acid of the invention, and functional analogs of the encoded protein, are essentially pure. For the purposes of this specification, "essentially pure" means that the protein and functional analogs are free from all but trace amounts of other proteins as well as of materials used during the purification process. A protein is considered to be essentially pure if it is at least 85%, preferably at least 90%, and more preferably at least 95% pure. Methods for purifying proteins are known in the art.

Determination of whether two amino acid sequences are substantially homologous is, for the purpose of the present specification, based on FASTA searches in accordance with Pearson et al. (1988). In the present specification, the amino acid sequence of a first protein is considered to be homologous to that of a second protein if the amino acid sequence of the first protein has at least about 20% amino acid sequence identity, preferably at least about 40% identity, and more preferably at least about 60% identity, with the sequence of the second protein. In the case of proteins having high homology, the amino acid sequence of the first protein has at least about 75% sequence identity, preferably at least about 85% identity, and more preferably at least about 95% identity, with the amino acid sequence of the second protein.

The protein encoded by the nucleic acid of the present invention further includes functional homologs. A protein is considered a functional homolog of another protein for a specific function, as described below, if the homolog has the same function as the other protein. The homolog can be, for example, a fragment of the protein, or a substitution, addition, or deletion mutant of the protein.

As is also known, it is possible to substitute amino acids in a sequence with equivalent amino acids. Groups of amino acids known normally to be equivalent are:

(a) Ala(A), Ser(S), Thr(T), Pro(P), Gly(G);
(b) Asn(N), Asp(D), Glu(E), Gln(Q);
(c) His(H), Arg(R), Lys(K);
(d) Met(M), Leu(L), Ile(I), Val(V); and
(e) Phe(F), Tyr(Y), Trp(W).

Substitutions, additions, and/or deletions in the amino acid sequences can be made as long as the protein encoded by the nucleic acid of the invention continues to satisfy the functional criteria described herein. An amino acid sequence that is substantially the same as another sequence, but that differs from the other sequence by means of one or more substitutions, additions, and/or deletions, is considered to be an equivalent sequence. Preferably, less than 50%, more preferably less than 25%, and still more preferably less than 10%, of the number of amino acid residues in a sequence are substituted for, added to, or deleted from the protein encoded by the nucleic acid of the invention.

As used herein, "progenitor cell" refers to any normal somatic cell that has the capacity to generate fully differentiated, functional progeny by differentiation and proliferation. Progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," the latter being defined as those cells that may or may not have the capacity to proliferate, i.e., self-replicate, but that are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include all the cells in a lineage of differentiation and proliferation prior to the most differentiated or the fully mature cell. Thus, for example, progenitors include the skin progenitor in the mature individual. The skin progenitor is capable of differentiation to only one type of cell, but is itself not fully mature or fully differentiated.

Production of some mature, functional blood cells results from proliferation and differentiation of "unipotential progenitors," i.e., those progenitors that have the capacity to make only one type of blood cell. For red blood cell (erythrocyte) production, a unipotential progenitor called a "CFU-E" (colony forming unit-erythroid) has the capacity to generate two to 32 mature progeny cells.

Various other hematopoietic progenitors have been characterized. For example, hematopoietic progenitor cells include those cells that are capable of successive cycles of differentiating and proliferating to yield up to eight different mature hematopoietic cell lineages. At the most primitive or undifferentiated end of the hematopoietic spectrum, hematopoietic progenitor cells include the hematopoietic "stem cells." These rare cells, which represent from about 1 in 10,000 to about 1 in 100,000 of the cells in the bone marrow, and the most primitive cells have the capacity to generate >$10^{13}$ mature blood cells of all lineages and are responsible for sustaining blood cell production over the life of an animal. They reside in the marrow primarily in a quiescent state, and may form identical daughter cells through a process called "self-renewal." Accordingly, such uncommitted progenitor cells can be described as being "totipotent," i.e., both necessary and sufficient for generating all types of mature blood cells. Progenitor cells that retain a capacity to generate all blood cell lineages but that can not self-renew are termed "pluripotent." Cells that can produce some but not all blood lineages and can not self-renew are termed "multipotent."

The protein encoded by the nucleic acid of the invention is useful to preserve any of these progenitor cells, including unipotent progenitor cells, pluripotent progenitor cells, multipotent progenitor cells, and/or totipotent progenitor cells. The protein is useful in the preservation and maintenance of progenitor cells in hematopoietic tissues as well as in non-hematopoietic tissues, such as those mentioned above.

The recombinant protein encoded by the nucleic acid of the invention is especially useful in preserving hematopoietic progenitors in mammals such as humans, mice, rats, etc. In the human, hematopoietic progenitor cells can be identified as belonging to a class of cells defined by their expression of a cell surface antigen designated CD34. These cells may be referred to as "CD34$^+$" cells. In the mouse, hematopoietic progenitor cells may be referred to as "Sca$^+$ Lin$^-$" cells, reflecting their cell surface antigen signature. Other mammalian species exhibit similar signature properties identifying hematopoietic progenitor cells. Hematopoietic progenitors can also be identified by their expression of the FLK2/FLT3 receptor.

Human hematopoietic progenitor cells that express the CD34 antigen and/or the FLK2/FLT3 receptor are referred to herein as "primitive progenitor cells." Therefore, primitive progenitor cells include CD34$^+$FLK2/FLT3$^-$ cells, CD34$^-$FLK2/FLT3$^+$ cells, and CD34$^+$FLK2/FLT3$^+$ cells. By contrast, hematopoietic cells that do not express either the CD34 antigen or the FLK2/FLT3 receptor (i.e., CD34$^-$FLK2/FLT3$^-$ cells) are referred to as "mature progenitor cells."

Preferably, the recombinant protein is effective to preserve progenitor cells that express the CD34 antigen and/or the FLK2/FLT3 receptor. The progenitor cells can include cells modified to express the CD34 antigen or FLK2/FLT3 receptors on their surface. In a preferred case, the protein has significant binding affinity for FLK2/FLT3 receptor on the cells, wherein binding of the protein with the FLK2/FLT3 receptor mediates the inhibition of differentiation of the cells. The protein encoded by the nucleic acid of the invention has been designated "FLK2/FLT3 Receptor-Interacting Lectin," abbreviated "FRIL," to describe this phenomenon, but this designator is used for convenience and should not be understood to definitionally ascribe any specific property to, or any origin of, the protein.

The recombinant protein mediates "preservation" of progenitor cells. By this is meant that the protein inhibits differentiation of the progenitor cells without depleting the progenitor cell population. In some cases, the inhibition of differentiation is accompanied by proliferation of the progenitor cell population. In other cases, the inhibition of differentiation is induced without proliferation of the progenitor cell population. In particular, by inhibiting differentiation processes, it is meant that the peptide significantly lowers the rate at which cells differentiate, and it may in fact completely stop these processes. While the mechanism by which the protein acts is not itself understood, one theoretical possibility is that the protein maintains progenitor cells in a quiescent or Go state of the cell cycle. Regardless of the actual mechanism of its action, however, the protein does preserve progenitor cells without killing the cells in significant numbers. In this sense, the recombinant protein is significantly distinguished from factors that inhibit or interfere with cellular processes (e.g., DNA replication, protein synthesis), and that thereby induce significant cell mortality.

As a result of the present invention, numerous utilities become technically feasible. The method of the invention can include contacting the progenitor cells with the recombinant protein in vitro, ex vivo, or in vivo. "In vitro" methods include methods such as laboratory experimental methods which are performed wholly outside a living body. While cells can be acquired from a living organism for use in vitro, it is understood that the cells will not be returned to the body. In vitro methods are commonly employed in experimental settings to advance understanding of particular systems. "Ex vivo" methods include clinical methods in which cells are manipulated outside the body of an organism, e.g., a patient, with the specific purpose of reimplanting some cells back into the organism to achieve a desired therapeutic purpose. "In vivo" methods are performed within the body of the organism, without requiring explantation or tissue sampling and manipulation.

For example, the recombinant protein finds a utility, inter alia, in that it enables ex vivo preservation of hematopoietic progenitor cells isolated from either normal or malignant (e.g., leukemic) bone marrow. Accordingly, the protein can be employed in the culture of mononuclear cells derived from a source of such cells, for example, from bone marrow, umbilical cord blood, placental blood, or peripheral blood. Alternatively, the recombinant protein can be used in conjunction with growth factors such as colony stimulating factors (CSFs) (e.g., IL3, GM-CSF, G-CSF, M-CSF), interleukins (e.g., IL1 through IL18) and KL in vitro to selectively induce proliferation and terminal differentiation of mature progenitors while preserving a significantly enriched population of primitive progenitors. U.S. Pat. Nos. 5,472,867 and 5,186,931 describe representative methods of using CSFs and interleukins (ILs) to expand progenitor cell populations in the contexts of, respectively, cancer chemotherapy and bone marrow transplants. In a preferred case according to the present invention, the method can further includes contacting the progenitor cells with FLK2/FLT3 ligand in an amount sufficient to selectively expand the number of progenitor cells without inducing differentiation thereof.

The recombinant protein also enhances survival of progenitor cells when cultured in vitro. For example, a process of in vitro selection can be used that involves using the protein to preserve progenitor cells in a substantially quiescent state in culture, while using a cytotoxic agent that exhibits selective toxicity for proliferating cells, e.g., to kill cells passing through cell cycle ("cycling cells"). Suitable cytotoxic agents include, for example, compounds such as adriamycin, cyclophosphamide, taxol or other taxane, cisplatin, 5-fluorouracil, and the like. The method is useful to preserve quiescent progenitor cells. The method is effective even when the progenitor cells are substantially free of stromal cells, which are considered to normally be necessary for progenitor cell maintenance and proper hematopoietic reconstitution. The recombinant protein improves the ability to functionally select stem cells either alone or with other factors. Such functional selection methods, include the method reported by Berardi et al. (1995) where selection is made using a combination of KL and IL3 with 5-FU.

By preserving progenitor cells in a quiescent state, the protein encoded by the nucleic acid of the invention preserves normal progenitor cells, while the cycling cells are killed. For example, ex vivo purging protocols can be used to selectively eliminate neoplastic cells by targeting the elimination of actively cycling cells. Once the progenitors cells have been purged of malignant cycling cells, they can be returned to the patient, and permitted to resume normal proliferation and differentiation. In one especially useful scenario, the recombinant protein allows for functional selection of normal progenitor cells from a leukemic bone marrow.

Such functional selection and purification of primitive stem cells can also be used to enable allogeneic transplant procedures. In situations where autologous tissue is not available for transplant, culturing allogeneic cells in the presence of the protein encoded by the nucleic acid of the invention will result in the selection of stem cells and depletion of T lymphocytes and other effector cells. This will enable transplant of progenitors while inhibiting a graft versus host reaction. Such stem cells acquire within the recipient immunological tolerance of the recipient's histocompatibility antigens.

It is a further advantage of the invention that it enables preservation of cells for periods and under conditions that permit shipment of cells, e.g., by mail, to distant locations for transplantation.

The recombinant protein also enables ex vivo manipulation of hematopoietic progenitor cells for use in gene therapy by preserving cells in liquid culture. For example, by preserving hematopoietic progenitor cells in culture for more than two weeks, the protein enables increased targeting efficiency by viral vectors that enter non-replicating cells (e.g., vectors such as adeno-associated viruses), and provides longer periods for the evaluation of the resultant cell populations to determine efficiency of transfection. Thus, in another embodiment, the method can be used in conjunction with methods of transfecting an exogenous DNA sequence into somatic cells. The method can then include transfecting progenitor cells selectively preserved by the recombinant protein.

The invention also has utility in conjunction with therapies, e.g., cancer therapies, which employ irradiation. Specifically, because the recombinant protein preserves progenitor cells in a quiescent state, administration of the recombinant protein to a mammalian subject in vivo allows the use of increased levels of total body irradiation to eliminate neoplastic cells, while leaving quiescent cells relatively unaffected. The protein can be employed in conjunction with other cytoprotective substances such as IL-1 to obtain an enhanced or complementary effect.

Thus, the method can involve treating a mammalian subject in need of hematopoietic therapy. In particular, the recombinant protein can be used to improve hematopoietic competence in a mammal, i.e., the mammal's ability to generate functional mature blood elements. For example, a tissue sample including hematopoietic progenitor cells can be obtained from the subject. Then the tissue sample can be cultured ex vivo in a growth medium containing the recombinant protein to preserve the progenitors, while allowing cycling cells to proliferate, differentiate and die. The cultured cells become significantly enriched in the primitive progenitor cells. Meanwhile, the mammal can be subjected to conditions sufficient to effect myeloablation, e.g., bone marrow irradiation, whole body irradiation, or chemically-induced myeloablation. Finally, the progenitor-enriched cultured cells can be administered or transfused to the mammal following the myeloablation to generate blood cellular components in the mammal, thereby reconstituting the hematopoietic system of the mammal. The method can use a tissue sample comprising peripheral blood, umbilical cord blood, placental blood, or bone marrow. Preferably, the tissue sample is autologous to the mammal. The tissue sample can also be at least substantially free of stromal cells.

While described here as an autologous procedure, the skilled practitioner will recognize that the methods can be readily adapted to transplant of progenitor-enriched cells from one individual to another. Again, when autologous tissue is not available for transplant, culturing allogeneic cells in the presence of the encoded protein can be used to induce selection of stem cells and depletion of T lymphocytes and other effector cells. The transplanted progenitor cells acquire within the recipient immunological tolerance of the recipient's histocompatibility antigens, thereby mitigating graft vs. host reactions.

The invention further includes a composition for preserving viability of progenitor cells ex vivo or in vitro. The composition comprises a culture medium suitable for growth and maintenance of mammalian cells in culture, along with an amount of the recombinant protein sufficient to preserve progenitor cells as described herein. Virtually any cell or tissue culture medium can be modified for the preservation of progenitors in this way. Suitable standardized culture media are known, including, for example, Minimum Essential Medium Eagle's (MEM), Dulbecco's Modified Eagle's Medium (DMEM), McCoy's 5A Modified Medium, Iscove's Modified Dulbecco's Medium (IMDM), Medium 199, RPMI-1640, specialized variant formulations of these media, and the like. Such media can be supplemented using sera (e.g., fetal bovine serum) buffers (e.g., HEPES), hormones, cytokines, growth factors, or other desired components. Numerous media are available commercially, e.g., from Sigma Chemical Co., St. Louis, Mo.

Ready-to-use receptacles, e.g., blood bags, media bags and bottles, microtiter plates, tissue and cell culture flasks, roller bottles, shake flasks, culture dishes, and the like, can also be provided with the protein encoded by the nucleic acid of the invention (with or without culture medium or other active components) to promote storage and/or culture of progenitor cells. The protein allows the artisan to store progenitor cells under refrigeration, at ambient temperature, or in an incubator at 37° C. The ability of the protein to preserve cells at ambient temperatures is particularly useful for transporting cells.

Also, the invention includes a method for preserving progenitor cells in a mammal in vivo. In this approach, the method comprises administering to the mammal the recombinant protein in an amount sufficient to preserve progenitor cells of the mammal in a substantially non-proliferative state. The mammal is then exposed to myeloablative conditions sufficient to effect ablation of proliferating myeloid cells but sparing non-proliferating progenitor cells. Following the ablative treatment, proliferation or differentiation of the preserved progenitor cells is reestablished, usually by administering to the mammal a cytokine in an amount sufficient to improve the viability of the progenitor cells. Preferred viability-improving cytokines include, for example, FLK2/FLT3 ligand, IL1, IL3, IL6, IL11, KL, or a combination thereof. According to this method, the recombinant protein can be used to enhance autologous bone marrow transplantation techniques in which lethal doses of radiation and/or chemotherapy are followed by reinfusion of stored marrow.

An effective amount of recombinant protein can be administered to a mammal by any convenient approach, such as parenteral routes, e.g., intravenous injection, or enteral routes, e.g., oral administration. Oral administration routes are expected to be useful since natural source lectins typically resist oral/gastric degradation, and can exhibit substantial bioavailability by this approach (Pusztai et al. 1995). The skilled artisan recognizes the utility and limitations of various methods of administration and can adjust dosage accordingly.

Other therapeutic utilities also present themselves to the skilled practitioner as being enabled by the invention. Such other utilities include, for example, expanding progenitor cell populations ex vivo to increase chances of engraftation, improving conditions for transporting and storing progenitor cells, and removing a fundamental barrier to enable gene therapy to treat and cure a broad range of life-limiting hematologic diseases such as sickle cell anemia and thalassemia.

The protein encoded by the nucleic acid of the invention can also be used as a specific probe for the identification or localization of progenitor cells. Since the protein binds specifically to primitive progenitor cells, a composition including the protein linked to a detectable moiety such as a fluorescent marker can be used to specifically label and identify progenitor cells. Thus, cell sorting to isolate progenitor cells can be performed, as can histologic localization of progenitor cells in tissues, and other methods known in the art. The skilled artisan can select the type or marker moiety to be employed and the method of isolating cells according to the task to be performed, since numerous methods of labeling proteins are known in the art.

The protein encoded by the nucleic acid of the invention can be used to isolate FLK2/FLT3-R-expressing progenitor cells. The protein is preferably linked to a chemical group or to an object to assist in the isolation. For example, the protein can be chemically linked to magnetic beads. The multivalent nature of the protein is particularly useful for isolation of cells, such as primitive hematopoietic progenitors, which express low levels of FLK2/FLT3-R (i.e., less than about 5,000 receptors/cell). Similar methods using antibodies linked to magnetic beads require significantly higher levels of cell surface receptors.

Making and Using the Nucleic Acid of the Invention

The nucleic acid sequence of the invention can be isolated from a natural source, such as being derived from legume plants. Legumes such as the garden pea or the common bean are plants ("leguminous plants") from a family (Leguminosae) of dicotyledonous herbs, shrubs, and trees bearing (nitrogen-fixing bacteria) nodules on their roots. These plants are commonly associated with their seeds (e.g., such as the garden pea or the common bean, etc.). More specifically, the nucleic acid can be isolated from members of the tribe Phaseoleae. In particular, the nucleic acid can be obtained from *Dolichos lab lab*, known as hyacinth beans and other common names throughout the world, from varieties of the common bean (*Phaseolus vulgaris*), e.g., red kidney beans, white kidney beans, etc., and from *Vigna sinensis*, commonly known as the black-eyed pea. In its native form isolated from such natural sources, the nucleic acid appears to encode a mannose/glucose-specific legume lectin. An exemplary isolation of the nucleic acid of the invention from *Dolichos lab lab* is described hereinbelow.

The entire gene or additional fragments of the gene are preferably isolated by using the known DNA sequence or a fragment thereof as a probe. To do so, restriction fragments from a genomic or cDNA library are identified by Southern hybridization using labeled oligonucleotide probes derived from SEQ ID NO:1.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together. See, generally, Sambrook et al. (1989) and Glover et al. (1995).

DNA expressing functional homologs of the protein can be prepared from wild-type DNA by site-directed mutagenesis. See, for example, Zoller et al. (1982); Zoller (1983); and Zoller (1984); McPherson (1991).

The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989). It is convenient to amplify the clones in the lambda-gt10 or lambda-gt11 vectors using lambda-gt10- or lambda-gt11-specific oligomers as the amplimers (available from Clontech, Palo Alto, Calif.).

Larger synthetic nucleic acid structures can also be manufactured having specific and recognizable utilities according to the invention. For example, vectors (e.g., recombinant expression vectors) are known which permit the incorporation of nucleic acids of interest for cloning and transformation of other cells. Thus, the invention further includes vectors (e.g., plasmids, phages, cosmids, etc.) which incorporate the nucleotide sequence of the invention, especially vectors which include the gene for expression of the protein encoded by the nucleic acid of the invention.

The DNA of the invention can be replicated and used to express recombinant protein following insertion into a wide variety of host cells in a wide variety of cloning and expression vectors. The host can be prokaryotic or eukaryotic. The DNA can be obtained from natural sources and, optionally, modified. The genes can also be synthesized in whole or in part.

Cloning vectors can comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13fd, and other filamentous single-stranded DNA phages.

Vectors for expressing proteins in bacteria, especially *E. coli*, are also known. Such vectors include the pK233 (or any of the tac family of plasmids), T7, and lambda $P_L$. Examples of vectors that express fusion proteins are PATH vectors described in Dieckmann and Tzagoloff (1985). These vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST). See., e.g., Smith (1988) and Abath (1990).

Vectors useful for cloning and expression in yeast are available. A suitable example is the 2$\mu$ circle plasmid.

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e., shuttle vectors, allow for the isolation and identification of protein coding sequences in prokaryotes.

Further eukaryotic expression vectors are known in the art (e.g., Southern et al. (1982); Subramani et al. (1981); Kaufmann et al. (1982); Kaufmann et al. (1982); Scahill et al. (1983); Urlaub et al. (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. coli* SG-936, *E. coli* HB101, *E. coli* W3110, *E. coli* X1776, *E. coli* X2282, *E. coli* DHI, and *E. coli* MRCl, Pseudomonas, Bacillus, such as *B. subtilis*, and Streptomyces. Suitable eukaryotic cells include yeasts and other fungi, insect, animal cells, such as COS cells and CHO cells, human cells and plant cells in tissue culture.

Fusion Proteins

The protein can be expressed in the form of a fusion protein with an appropriate fusion partner. The fusion partner preferably facilitates purification and identification. Increased yields can be achieved when the fusion partner is expressed naturally in the host cell. Some useful fusion partners include beta-galactosidase (Gray et al. 1982); trpE (Itakura et al. 1977); protein A (Uhlen et al. 1983); glutathione S-transferase (Johnson 1989; Van Etten et al. 1989); and maltose binding protein (Guan et al. 1987; Maina et al. 1988; Riggs 1990).

Such fusion proteins can be purified by affinity chromatography using reagents that bind to the fusion partner. The reagent can be a specific ligand of the fusion partner or an antibody, preferably a monoclonal antibody. For example, fusion proteins containing beta-galactosidase can be purified by affinity chromatography using an anti-beta-galactosidase antibody column (Ullman 1984). Similarly, fusion proteins containing maltose binding protein can be purified by affinity chromatography using a column containing cross-linked amylose; see Guan, European Patent Application 286,239, incorporated herein by reference.

Optionally, the DNA that encodes the fusion protein is engineered so that the fusion protein contains a cleavable site between the protein and the fusion partner. The protein can occur at the amino-terminal or the carboxy-terminal side of the cleavage site. Both chemical and enzymatic cleavable sites are known in the art. Suitable examples of sites that are cleavable enzymatically include sites that are specifically recognized and cleaved by collagenase (Keil et al. 1975); enterokinase (Hopp et al. 1988); factor Xa (Nagai et al. 1987); and thrombin (Eaton et al. 1986). Collagenase cleaves between proline and X in the sequence Pro-X-Gly-Pro wherein X is a neutral amino acid. Enterokinase cleaves after lysine in the sequence Asp-Asp-Asp-Asp-Lys. Factor Xa cleaves after arginine in the sequence Ile-Glu-Gly-Arg. Thrombin cleaves between arginine and glycine in the sequence Arg-Gly-Ser-Pro.

Specific chemical cleavage agents are also known. For example, cyanogen bromide cleaves at methionine residues in proteins.

The recombinant protein is purified by methods known in the art. Such methods include affinity chromatography using specific antibodies. Alternatively, the recombinant protein can be purified using a combination of ion-exchange, size-exclusion, and hydrophobic interaction chromatography using methods known in the art. These and other suitable methods are described, e.g., in Marston (1987).

Mixtures of proteins can be separated by, for example, SDS-PAGE in accordance with the method of Laemmli (1970). The molecular weights were determined by resolving single bands on SDS-PAGE and comparing their positions to those of known standards. The method is understood by those in the art to be accurate within a range of 3–5%. Molecular weights can vary slightly between determinations.

Fragments and Probes

As noted, the invention also includes fragments of the nucleic acid specified as SEQ ID NO:1. Such fragments include primers and probes which are useful as tools in numerous molecular engineering techniques. The fragment can be used as a primer ("amplimer") to selectively amplify nucleic acid, such as genomic DNA, total RNA, etc. The fragment can also be an oligonucleotide complementary to a target nucleic acid molecule, i.e., the fragment can be a probe. In either case, the oligonucleotide can be RNA or DNA. The length of the oligonucleotide is not critical, as long as it is capable of hybridizing to the target molecule. The oligonucleotide should contain at least 6 nucleotides, preferably at least 10 nucleotides, and, more preferably, at least 15 nucleotides. There is no upper limit to the length of the oligonucleotide. Longer fragments are more difficult to prepare and require longer hybridization times. Therefore, the oligonucleotide should not be longer than necessary. Normally, the oligonucleotide will not contain more than 50 nucleotides, preferably not more than 40 nucleotides, and, more preferably, not more than 30 nucleotides.

Methods for determining whether a probe nucleic acid molecule recognizes a specific target nucleic acid molecule in a sample are known in the art. Generally, a labeled probe that is complementary to a nucleic acid sequence suspected of being in a sample is prepared. Preferably, the target nucleic acid molecule is immobilized. The presence of probe hybridized to the target nucleic acid molecule indicates the presence of the nucleic acid molecule in the sample. Examples of suitable assay methods are described in Dallas et al. (1975); Grunstein et al. (1975); U.S. Pat. No. 4,731,325, U.S. Pat. No. 4,683,195, U.S. Pat. No. 4,882,269, and PCT publication WO 90/01069, all of which are incorporated herein by reference.

The probes described above are labeled in accordance with methods known in the art. The label can be a radioactive atom, an enzyme, or a chromophoric moiety.

Methods for labeling oligonucleotide probes have been described, for example, in Leary et al. (1983); Renz et al. (1984); Richardson et al. (1983); Smith et al. (1985); and Meinkoth et al. (1984).

The label can be radioactive. Some examples of useful radioactive labels include $^{32}P$, $^{125}I$, $^{131}I$, and $^{3}H$. Use of radioactive labels have been described in U.K. patent document 2,034,323, and U.S. Pat. Nos. 4,358,535, and 4,302,204, each incorporated herein by reference.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, and EP 63,879, each incorporated herein by reference, and by Rotman (1961).

Useful chromophores include, for example, fluorescent, chemiluminescent, and biolurninescent molecules, as well as dyes. Some specific chromophores useful in the present invention include, for example, fluorescein, rhodamine, Texas red, phycoerythrin, umbelliferone, luminol.

The labels can be conjugated to the antibody or nucleotide probe by methods that are well known in the art. The labels can be directly attached through a functional group on the probe. The probe either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules can be conjugated to the antibodies or nucleotides by means of coupling agents, such as dialdehydes, carbodiimides, dimaleimides, and the like.

The label can also be conjugated to the probe by means of a ligand attached to the probe by a method described above and a receptor for that ligand attached to the label. Any of the known ligand-receptor combinations is suitable. Some suitable ligand-receptor pairs include, for example, biotin-avidin or -streptavidin, and antibody-antigen. The biotin-avidin combination is preferred.

In any case, methods for making and using nucleic acid probes are well documented in the art. For example, see Keller et al. (1993) and Hames et al. (1995).

The following examples are provided to assist in a further understanding of the invention. The particular materials and conditions employed are intended to be further illustrative of the invention and are not limiting upon the reasonable scope thereof.

EXAMPLE 1

RNA Isolation and cDNA Synthesis

Total RNA was prepared from mid-maturation *Dolichos lab lab* seeds stored at −70° C. following the procedure of Pawloski et al. (1994). Poly ($A^+$) RNA was obtained from this total RNA using the mRNA Isolation System (Promega) sold under the trademark, POLYATRACT, according to the manufacturer's instructions. Avian myeloblastosis virus reverse transcriptase (Promega) was used to generate cDNA from 0.5 μg poly($A^+$)RNA, or from 3.0 μg of total RNA, using 1 μg of oligo(dT) in standard reaction conditions (Sambrook et al. 1989).

Polymerase Chain Reaction and cDNA Cloning

EXAMPLE 2A

Based on the amino acid sequence published by Gowda et al. (1994), two degenerate oligonucleotide primers were designed using Phaseolus codon usage (Devereux et al. 1984):

MLA AA(AG)TT(TC)GA(TC)CC(AT)AA(TC)CA(AG)GA(AG)GA (SEQ ID NO:3)

MLZ TT(AT)CC(AG)TT(TC)TGCCA(AG)TCCCA (SEQ ID NO:4)

A 500+ bp product was amplified from cDNA prepared as described in Example 1, by 30 cycles of polymerase chain reaction (PCR), each cycle comprising 40 s at 94° C., 40 s at 50° C., 60 s at 72° C., followed by an extension step at 72° C. for 10 min. Reactions were performed in 50 μL containing 30 pmol of each primer, 0.2 mM deoxyribonucleotides and 0.5 unit of the Taq polymerase (Perkin Elmer) sold under the trademark, AMPLITAQ, in the corresponding buffer.

The 500 bp product obtained by PCR was cloned in the cloning vector, pCR2.1 (Invitrogen), and sequenced by sequenase dideoxy chain termination (United States Biochemicals) using the following primers:

GTACCGAGCTCGGAT (SEQ ID NO:5)

TCTAGATGCATGCTCGAG (SEQ ID NO:6).

This sequence was designated "FRILa," as relating to the gene encoding the protein of interest, designated "FRIL" as noted above.

EXAMPLE 2B

Based on the sequence of the FRILa amplified product, a specific primer was prepared:

MLX GTTGGACGTCAATTCCGATGTG (SEQ ID NO:7)

A degenerate primer corresponding to the first five amino acids of the sequence published by Gowda et al. (1994) was also prepared:

MLI GC (TC) CA (AG) TC (TC) CT (TC) TC (TC) TT (SEQ ID NO:8)

The MLX and MLI primers were used in combination to amplify a 480 bp product from cDNA prepared as in Example 1, through 30 PCR cycles using the same conditions described above. This secondary amplified fragment was cloned in the pCR2.1 vector and sequenced as described above, and was designated "FRILb."

EXAMPLE 2C

The 3' end of FRIL was obtained through rapid amplification of cDNA ends by polymerase chain reaction (RACE-PCR) (see, e.g., Frohman 1990) using the 5'/3' RACEKIT (Boehringer Mannheim) according to the manufacturer's instructions. In the cDNA synthesis for the 3' RACE, an oligo(dT) anchor primer ("AP") supplied with the kit was used, at a concentration of 32.5 μM, using the standard conditions described above in Example 1.

AP GACCACGCGTATCGATGTCGAC (SEQ ID NO:9)

Nested PCR amplifications were performed using the AP anchor primer in combination with a specific primer having the following sequence:

MLB AAGTTAGACAGTGCAGGAAAC (SEQ ID NO:10). The amplification conditions were again 30 cycles of 40 s at 94° C., 40 s at 55° C., 60 s at 72° C. each, with an extension step at 72° C. for 10 min. A 900+ bp product was obtained, which was subcloned in pCR2.1 and sequenced as described above, and was designated "FRILc" (SEQIDNO:1).

EXAMPLE 2D

To obtain the full length cDNA clone, the anchor primer AP was used in combination with a specific primer corresponding to the first 5 amino acids encoded at the 5'-terminus:

MLII GCACAGTCATTGTCATTTAG (SEQ ID NO:11).

The full length cDNA was obtained through 30 cycles of PCR, each cycle comprising 60 s at 94° C., 60 s at 58° C., 90 s at 72° C., with an extension step at 72° C. for 10 min. The reaction was performed in 100 μL containing 30 pmol of each primer, 0.2 mM deoxyribonucleotide, 1.0 unit of Pfu polymerase (Stratagene). The MLII and AP primers were designed to generate an EcoRI site at each end (3' and 5') of the polynucleotide sequence. The full length cDNA was ligated into the EcoRI site of the cloning vector pCR2.1, resulting in the final product "pCR2.1-DLA" illustrated schematically in FIG. 1.

EXAMPLE 3

The Nucleotide Sequence of FRIL

The FRILc clone obtained as described in Example 2C was sequenced completely using the dideoxy chain termination method. The nucleotide sequence of the full-length cDNA is:

```
  1 GCACAGTCAT TGTCATTTAG TTTCACCAAG TTTGATCCTA ACCAAGAGGA (SEQ ID NO:1)
 51 TCTTATCTTC CAAGGTCATG CCACTTCTAC AAACAATGTC TTACAAGTCA
101 CCAAGTTAGA CAGTGCAGGA AACCCTGTGA GTTCTAGTGC GGGAAGAGTG
151 TTATATTCTG CACCATTGCG CCTTTGGGAA GACTCTGCGG TATTGACAAG
201 CTTTGACACC ATTATCAACT TGAAATCTC AACACCTTAC ACTTCTCGTA
251 TAGCTGATGG CTTGGCCTTC TTCATTGCAC CACCTGACTC TGTCATCAGT
301 TATCATGGTG GTTTTCTTGG ACTCTTTCCC AACGCAAACA CTCTCAACAA
351 CTCTTCCACC TCTGAAAACC AAACCACCAC TAAGGCTGCA TCAAGCAACG
401 TTGTTGCTGT TGAATTTGAC ACCTATCTTA ATCCCGATTA TGGTGATCCA
451 AACTACATAC ACATCGGAAT TGACGTCAAC TCTATTAGAT CCAAGGTAAC
501 TGCTAAGTGG GACTGGCAAA ATGGGAAAAT AGCCACTGCA CACATTAGCT
551 ATAACTCTGT CTCTAAAAGA CTATCTGTTA CTAGTTATTA TGCTGGGAGT
601 AAACCTGCGA CTCTCTCCTA TGATATTGAG TTACATACAG TGCTTCCTGA
651 ATGGGTCAGA GTAGGGTTAT CTGCTTCAAC TGGACAAGAT AAAGAAAGAA
701 ATACCGTTCA CTCATGGTCT TTCACTTCAA GCTTGTGGAC CAATGTGGCG
751 AAGAAGGAGA ATGAAAACAA GTATATTACA AGAGGCGTTC TGTGATGATA
801 TATGTGTATC AATGATTTTC TATGTTATAA GCATGTAATG TGCGATGAGT
851 CAATAATCAC AAGTACAGTG TAGTACTTGT ATGTTGTTTG TGTAAGAGTC
901 AGTTTGCTTT TAATAATAAC AAGTGCAGTT AGTACTTGT
```

The FRIL nucleotide sequence enabled inference of a derived amino acid sequence for the FRIL protein:

```
AQSLSFSFTK FDPNQEDLIF QGHATSTNNV LQVTKLDSAG NPVSSSAGRV (SEQ ID NO:2)

LYSAPLRLWE DSAVLTSFDT IINFEISTPY TSRIADGLAF FIAPPDSVIS

YHGGFLGLFP NANTLNNSST SENQTTTKAA SSNVVAVEFD TYLNPDYGDP

NYIHIGIDVN SIRSKVTAKW DWQNGKIATA HISYNSVSKR LSVTSYYAGS

KPATLSYDIE LHTVLPEWVR VGLSASTGQD KERNTVHSWS FTSSLWTNVA

KKENENKYIT RGVL
```

A comparative illustration of the derived FRIL amino acid sequence with the reported amino acid sequence of the mannose lectin as determined by Gowda et al. (1994) is shown in FIG. 2. The single sequence derived for FRIL protein comprises domains that correspond directly and with substantial homology to the α subunit (SEQ ID NO:12) and β subunit (SEQ ID NO:13) of the protein described by Gowda et al. (1994). When the β subunit of the Gowda et al. protein is assigned to the N-terminal domain and is followed linearly by the α subunit, the arrangement of the polypeptides shows homology to other legume lectins. However, the derived FRIL amino acid sequence comprises an insert of seven amino acid residues (aa27–34) that does not occur in the protein described by Gowda et al. Several other differences between the amino acid sequences of the two proteins are also readily discernible from FIG. 2.

EXAMPLE 4

Site-Specific Mutagenesis

To establish functionality of homologs of the protein encoded by the FRIL cDNA, a mutation was made in the FRIL cDNA clone. The domains of the derived protein and the pea lectin that include the mutation site are shown below:

FRIL . Y L N P D Y G . D P N Y I H I G I D V (SEQ ID NO:14)

Pea F Y . N A A W D P S N R D R H I G I D V (SEQ ID NO:15)

It is known that the asparagine residue (the highlighted "N") in the pea lectin is involved in binding to its saccharide ligand. The corresponding asparagine in FRIL (position 141 of the amino acid sequence, based on the sequence including the 15 amino acid signal peptide) was mutated to aspartic acid ("D"). This mutation was designated "N141D" for convenience.

To introduce the mutation, recombinant PCR was performed (Higuchi 1990). Two PCR reactions were carried out separately on the full length cDNA using two primers that contain the same mutation and produce two products with an overlapping region:

MutI CCATAATCGGGATCAAGATAGGTG (SEQ ID NO:16)

MutII CACCTATCTTGATCCCGATTATGG (SEQ ID NO:17)

The primary PCR products were purified with the QIAquick PCR Purification kit (QIAGEN), according to the manufacturer's instructions. The overlapping primary products were then combined and amplified together in a single second reaction using flanking primers:

M1 Forw AACTCAGCCGCACAGTCATTGTCA (SEQ ID NO:18)

APEcoRI GAATTCGACCACGCGTATCGATGTCGAC (SEQ ID NO:19)

Both the primary and the secondary PCR reactions were performed in 100 µL containing 50 pmol of each primer, 0.4 mM deoxyribonucleotide and 1.0 unit Pfu polymerase (Stratagene) in the corresponding buffer. The primary PCR reaction amplified the two separate fragments in 30 cycles, each cycle comprising 40 s at 94° C, 40 s at 50° C., 72° C. 60 s, with an extension step at 72° C. for 10 min. The second PCR reaction amplified the recombinant fragment in 12 cycles using the same conditions reported above.

Figure 3:
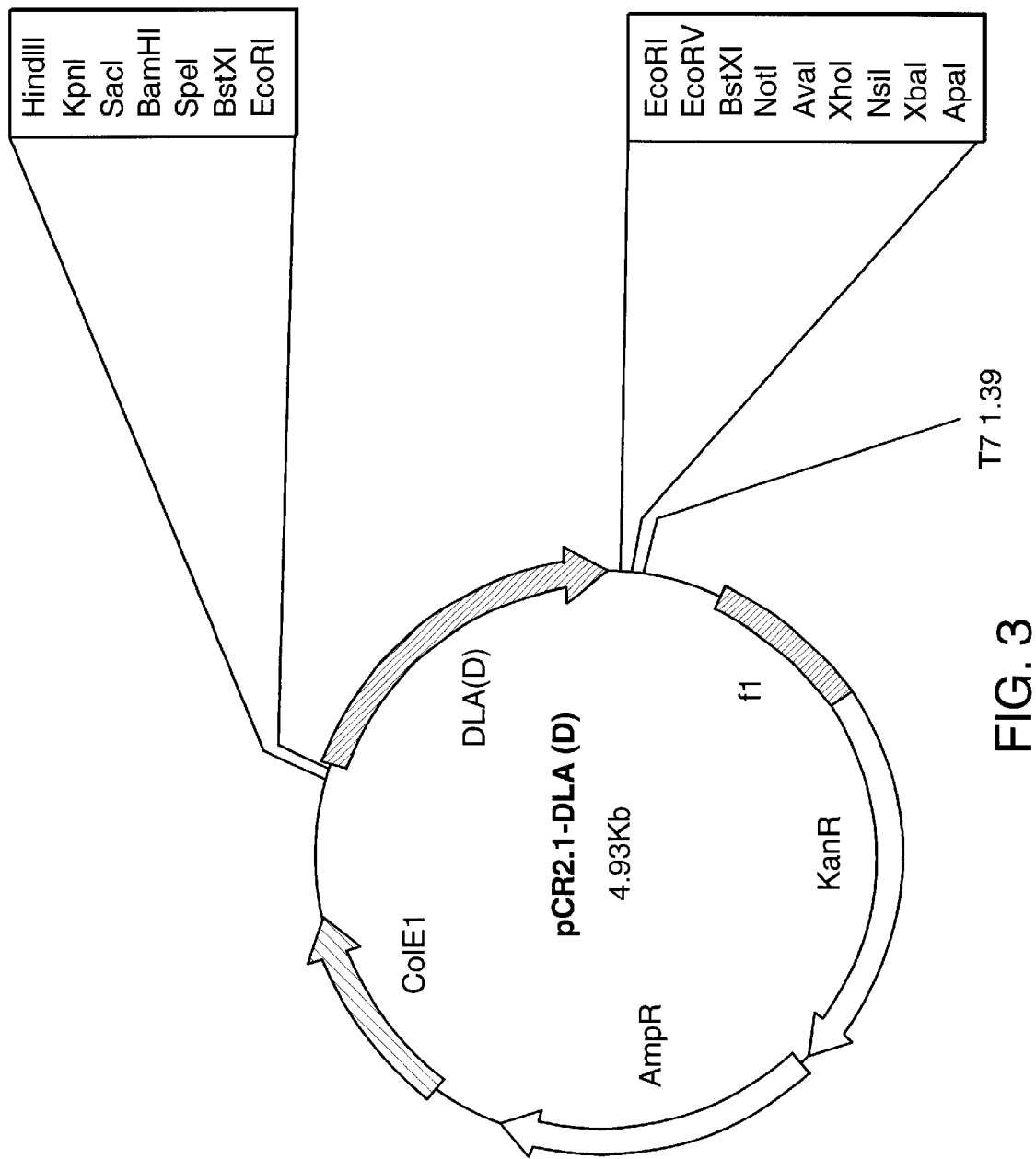
FIG. 3 is a map of a cloning vector pCR2.1-DLA(D) manufactured by ligating a mutated cDNA in the EcoRI site of the cloning vector pCR2.1.

The resulting full-length fragment contained the mutation. The recombinant mutated product was cloned in the EcoRI site of the cloning vector pCR2.1, as illustrated schematically in FIG. 3, and sequenced as described above. This plasmid is referred to as "pCR2.1-DLA(D)."

EXAMPLE 5

Construction of Plant Expression Vectors and *Nicotiana tabacum* Transformation Recombinant PCR was used to modify the 5' ends of both the wild-type and the mutant FRIL clones, to introduce a signal peptide for entry of the protein into the endoplasmic reticulum. Following the procedure of Higuchi (1990), the sequence encoding the signal peptide and the full-length cDNA clones were amplified in two separate primary PCR reactions. The signal peptide sequence was obtained from the amplification of the binary vector pTA4, harboring the complete sequence of the α-amylase inhibitor gene (Hoffman et al. 1982; Moreno et al. 1989).

The following primers were used for amplification of the signal peptide sequence:

Sigforw GAATTCATGGCTTCCTCCAAC (SEQ ID NO:20)

Sigrev TGACTGTGCGGCTGAGTTTGCGTGGGTG (SEQ ID NO:21)

The primers M1Forw (SEQ ID NO:18) and APEcoRI (SEQ ID NO:19) used for amplification of the FRIL cDNA in Example 4 above, were again used to amplify the FRIL cDNA.

The primers used for the secondary reactions were Sigforw and APEcoRI, which were designed to generate EcoRI sites at the 5' and the 3' ends. Both the primary and the secondary PCR reactions were performed as discussed above for the site-directed mutagenesis.

Figure 4:
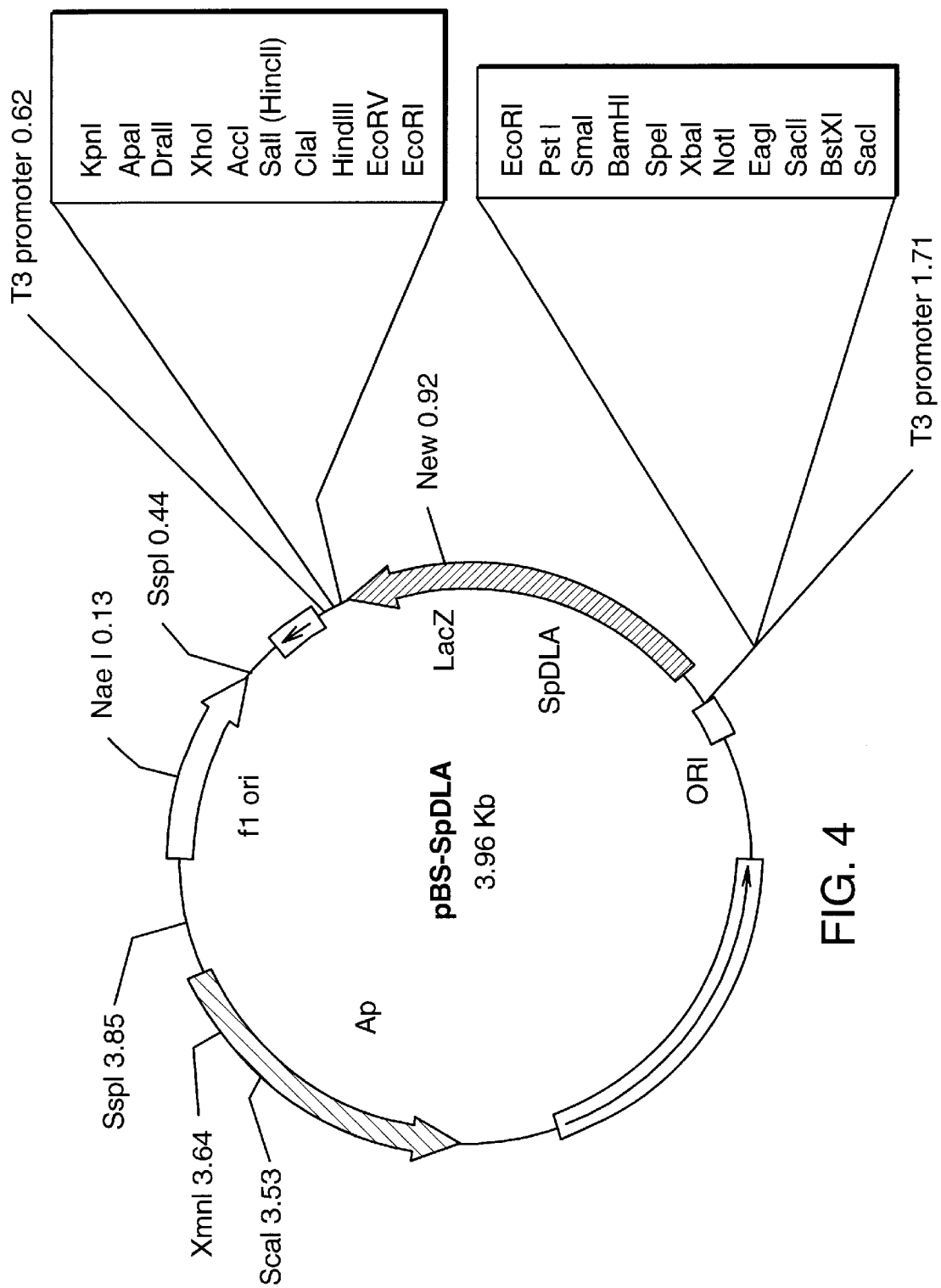
FIG. 4 is a map of a cloning vector pBS-SpDLA manufactured by ligating a recombinant fragment in the EcoRI site of the cloning vector pBluescript SK+.
Figure 5:
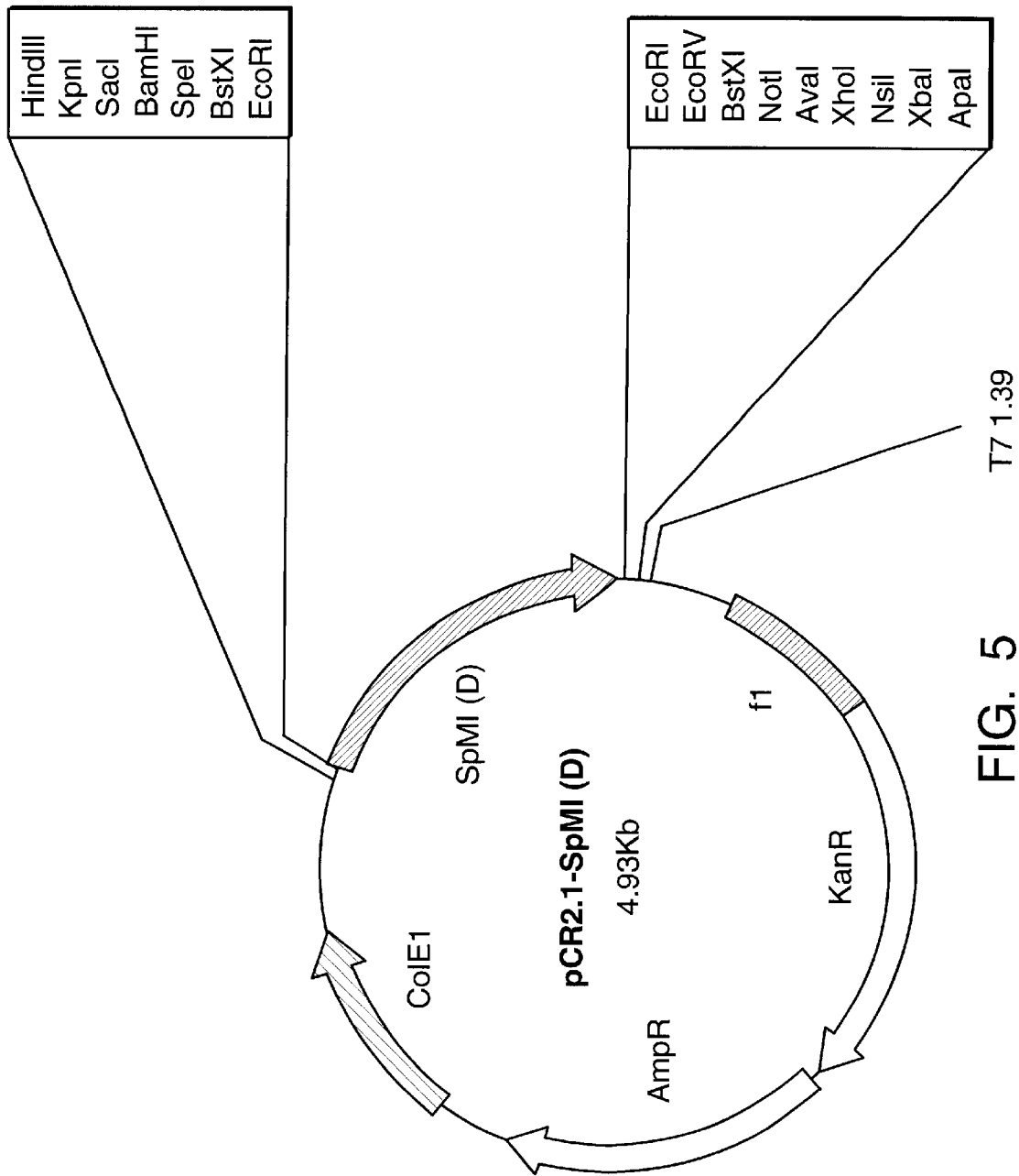
FIG. 5 is a map of a cloning vector pCR2.1-SpM1(D) manufactured by ligating a mutated recombinant clone in the EcoRI site of the cloning vector pCR2.1.

The wild-type recombinant product SpDLA was cloned in the EcoRI site of the pBluescript SK+ cloning vector (Stratagene) to give the vector pBS-SpDLA, as shown in FIG. 4. The mutant SpDLA(D) was cloned in the same site of the cloning vector pCR2.1 to give the vector pCR2.1-SpM1, as shown in FIG. 5. The nucleotide sequence of each PCR product was determined as described above to verify the correct attachment of the signal peptide. The nucleotide sequence of SpDLA is defined by SEQ ID NO:22, and the derived amino acid sequence is defined by SEQ ID NO:23.

EXAMPLE 6

Figure 6:
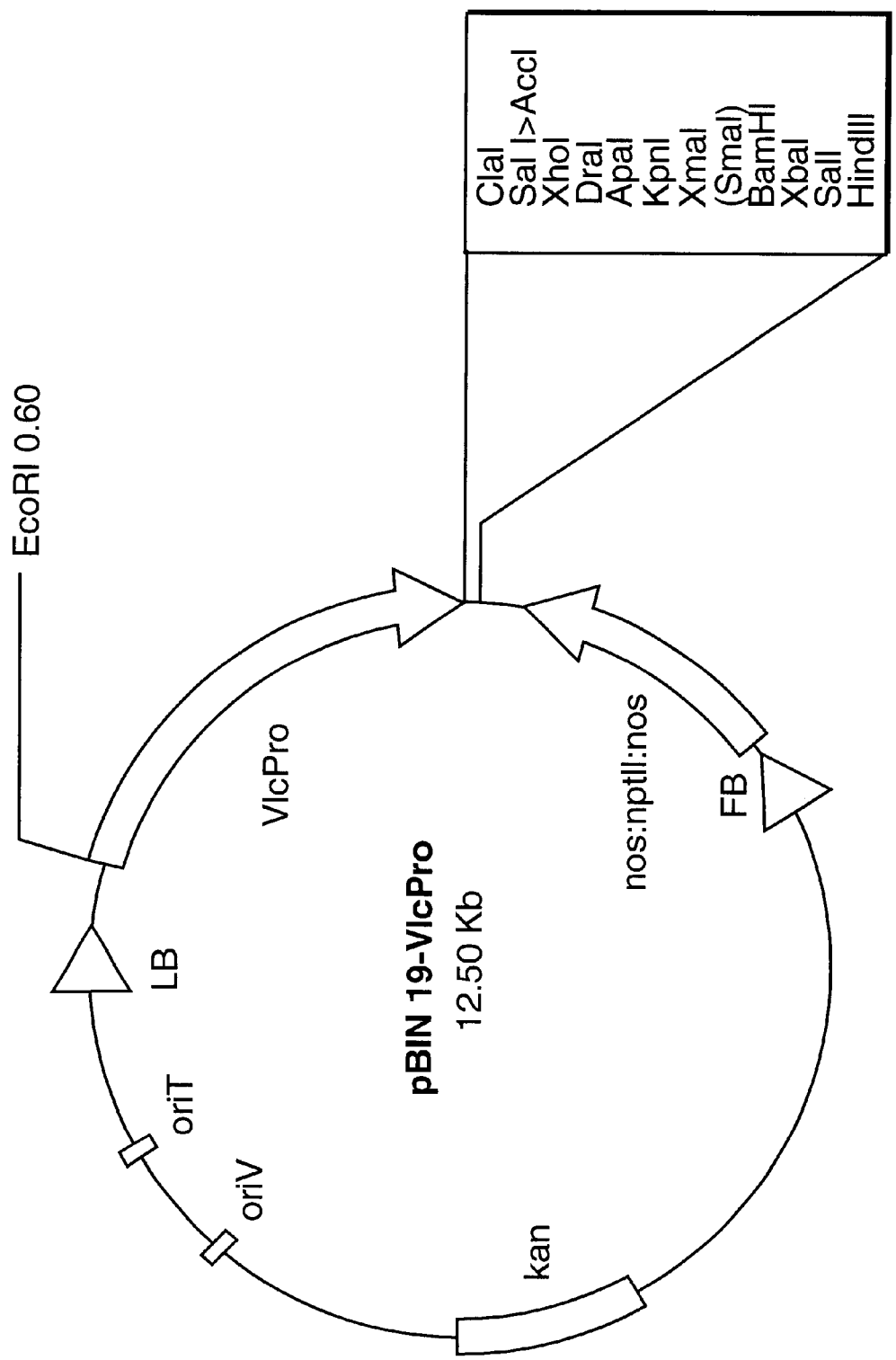
FIG. 6 is a map of a recombinant expression vector pBIN-VicPro manufactured by subcloning the vicilin promoter obtained from the pCW66 vector in the EcoRI/ClaI site of the plant binary vector pBIN19 for Agrobacterium-mediated transformation.
Figure 7:
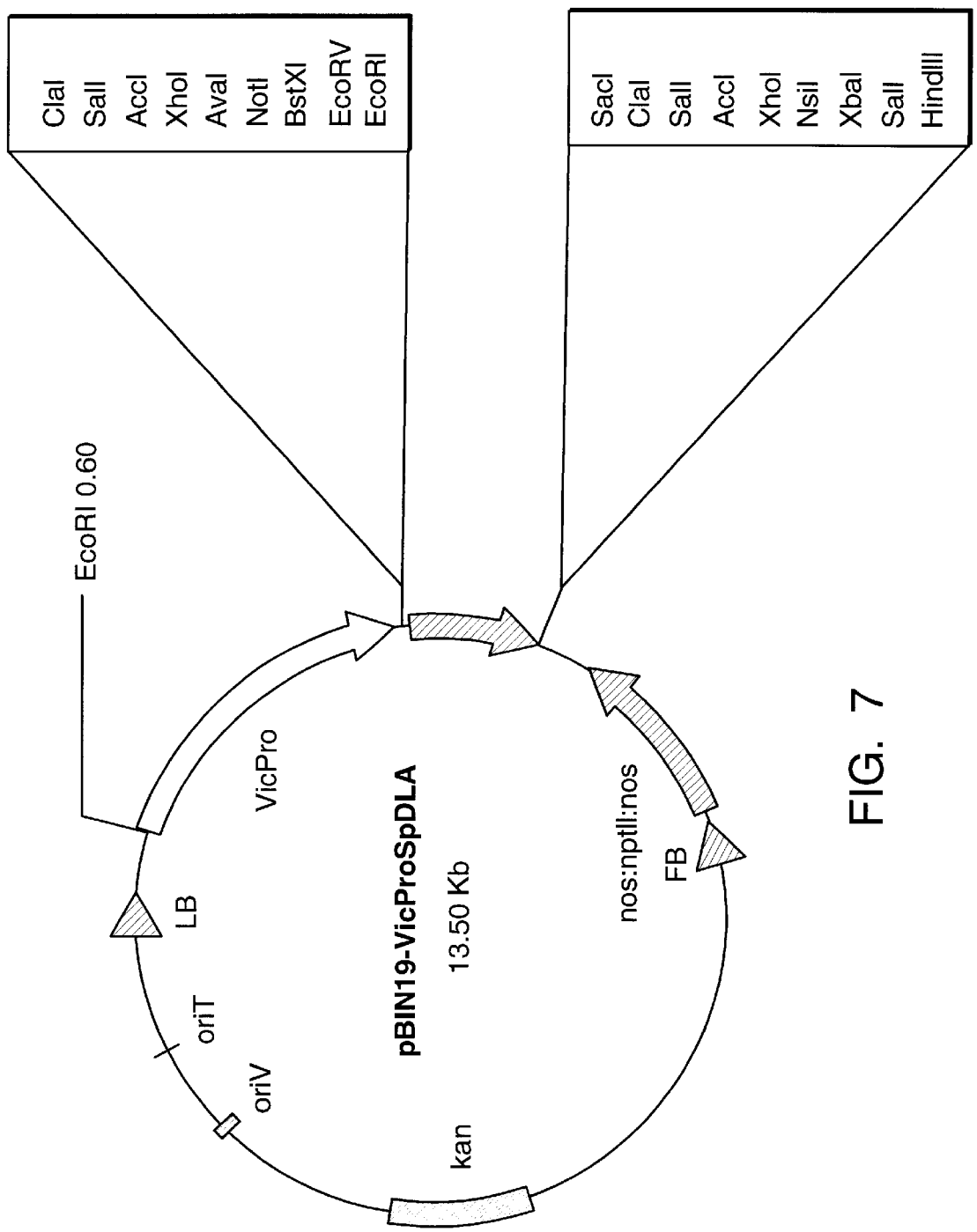
FIG. 7 is a map of a recombinant expression vector pBINVicPro-SpDLA manufactured by ligating a recombinant fragment in the EcoRI/SacI site of the pBINVicPro vector.
Figure 8:
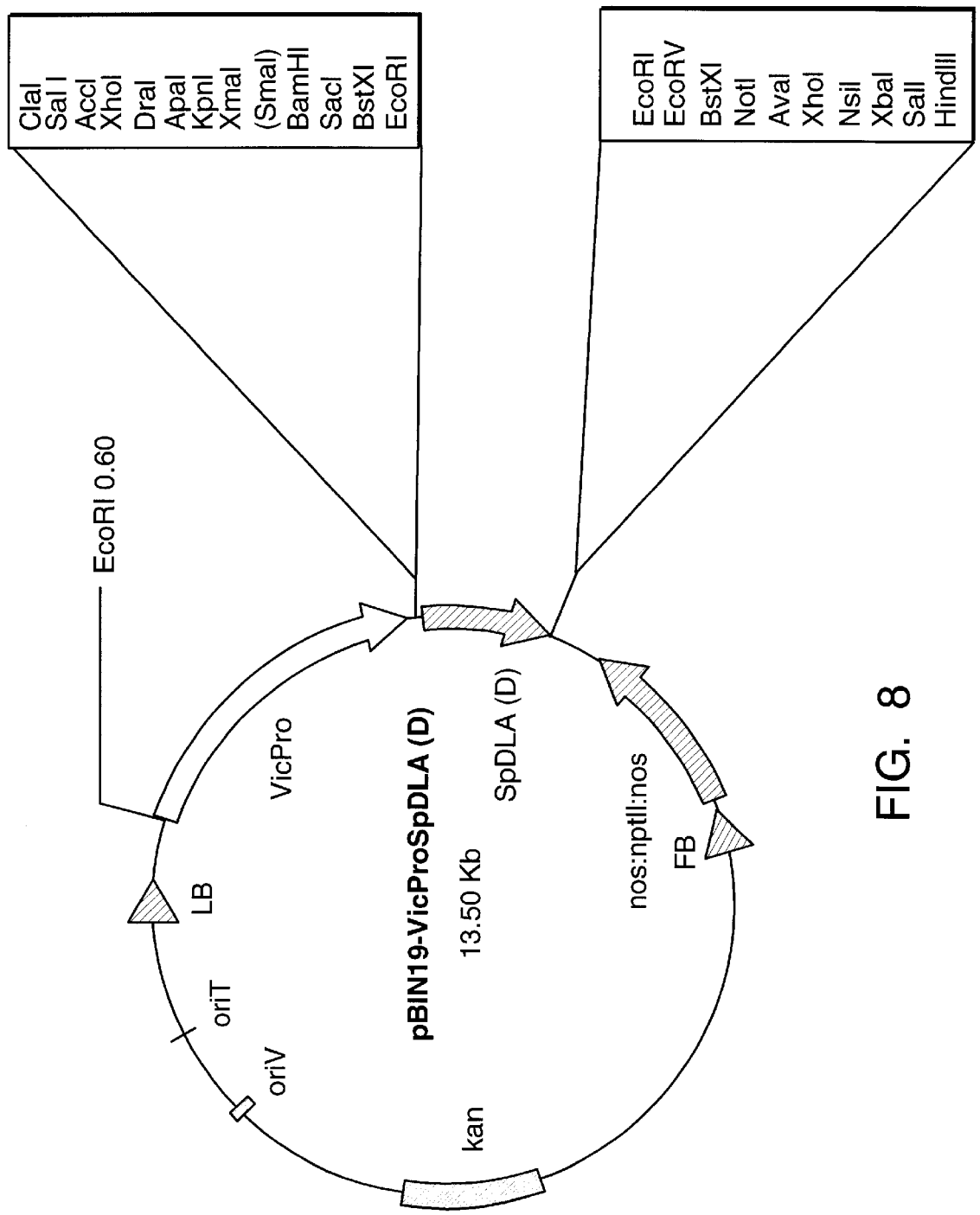
FIG. 8 is a map of a recombinant expression vector pBINVicPro-SpDLA(D) manufactured by ligating a mutated recombinant clone in the EcoRI site of the pBIN-VicPro vector.

A binary vector was constructed for seed-specific expression of FRIL. For seed expression, the vicilin promoter obtained from the pCW66 (Higgins at al. 1988) was cloned in EcoRI/KpnI sites of the plant expression vector pBIN19, to form pBINVicPro, as illustrated in FIG. 6. Downstream of the vicilin promoter, the SpDLA cDNA sequence was ligated into the EcoRI/SacI site giving rise to the pBINVicPro-SpDLA, which is illustrated in FIG. 7. The mutated cDNA clone SpDLA(D) was ligated in EcoRI site of the pBINVicPro vector to yield pBINVicPro-SpDLA(D), which is illustrated in FIG. 8. No additional termination sequences were added, relying instead on the stop codons and the polyadenylation site of the DLA and DLA(D) cDNA clones. Both vectors were transferred into *Agrobacterium tumefaciens* strain LBA4404 according to the freeze-thaw procedure reported by An et al. (1988).

Figure 9:
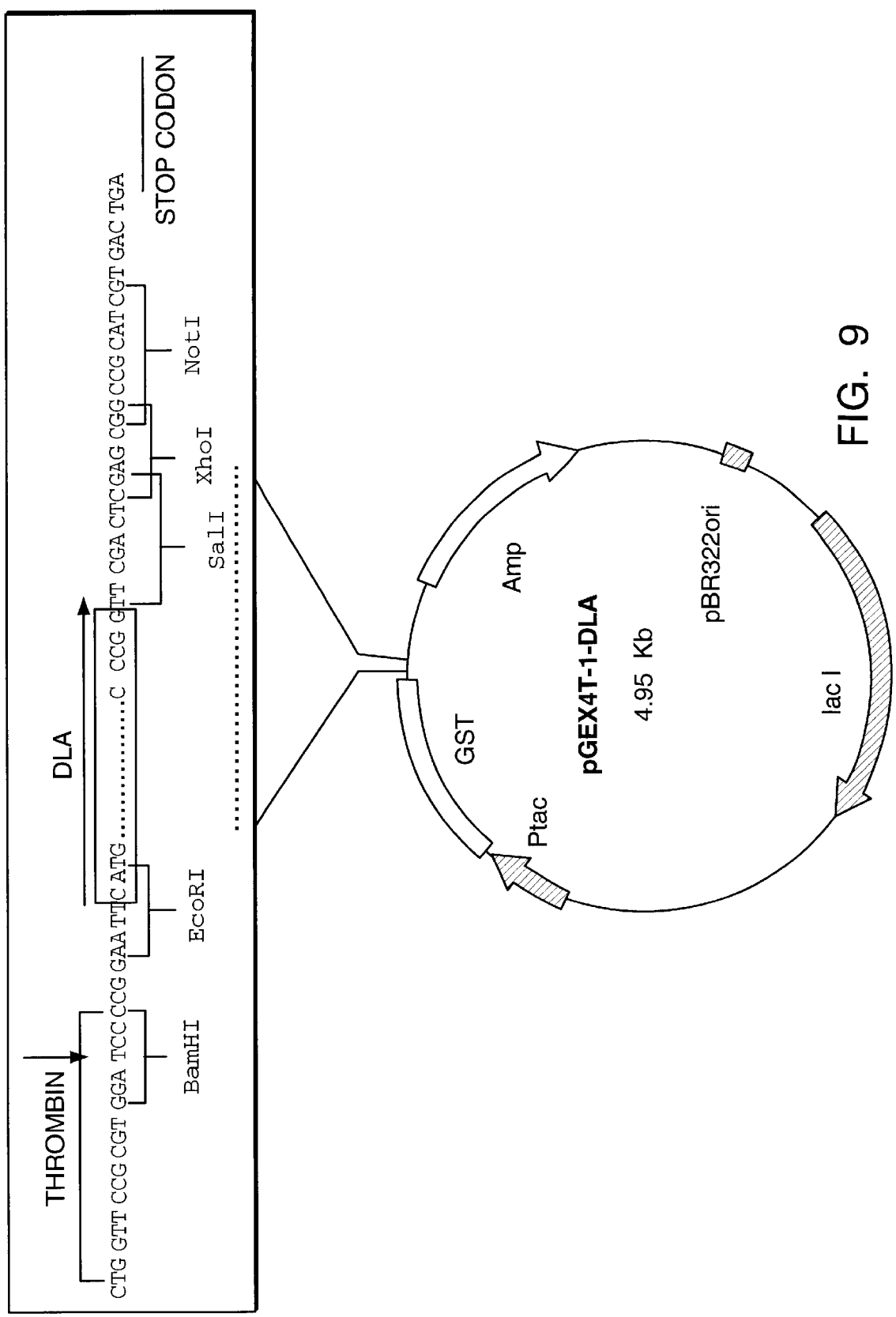
FIG. 9 is a map of a recombinant expression vector pGEX4T-1-DLA manufactured by ligating a wild-type cDNA clone in the EcoRI/SalI site of the E. coli expression vector pGEX4T-1.

Agrobacterium-mediated transformation of *Nicotiana tabacum* leaf disks was carried out and assayed as described (Horsch et al. 1985) using LBA4404 harboring the seed-specific expression vector pBINVicPro-SpDLA (FIG. 9). Kanamycin-resistant plants (resistance being conferred by transformation with the pBIN19-based vectors that carry the gene) were scored for their ability to form roots in two consecutive steps of propagation in Murashige-Skoog medium containing 3% of sucrose and kanamycin sulfate (Sigma) 100 mg/mL.

EXAMPLE 7

Expression of Recombinant FRIL in *E. coli*

Figure 10:
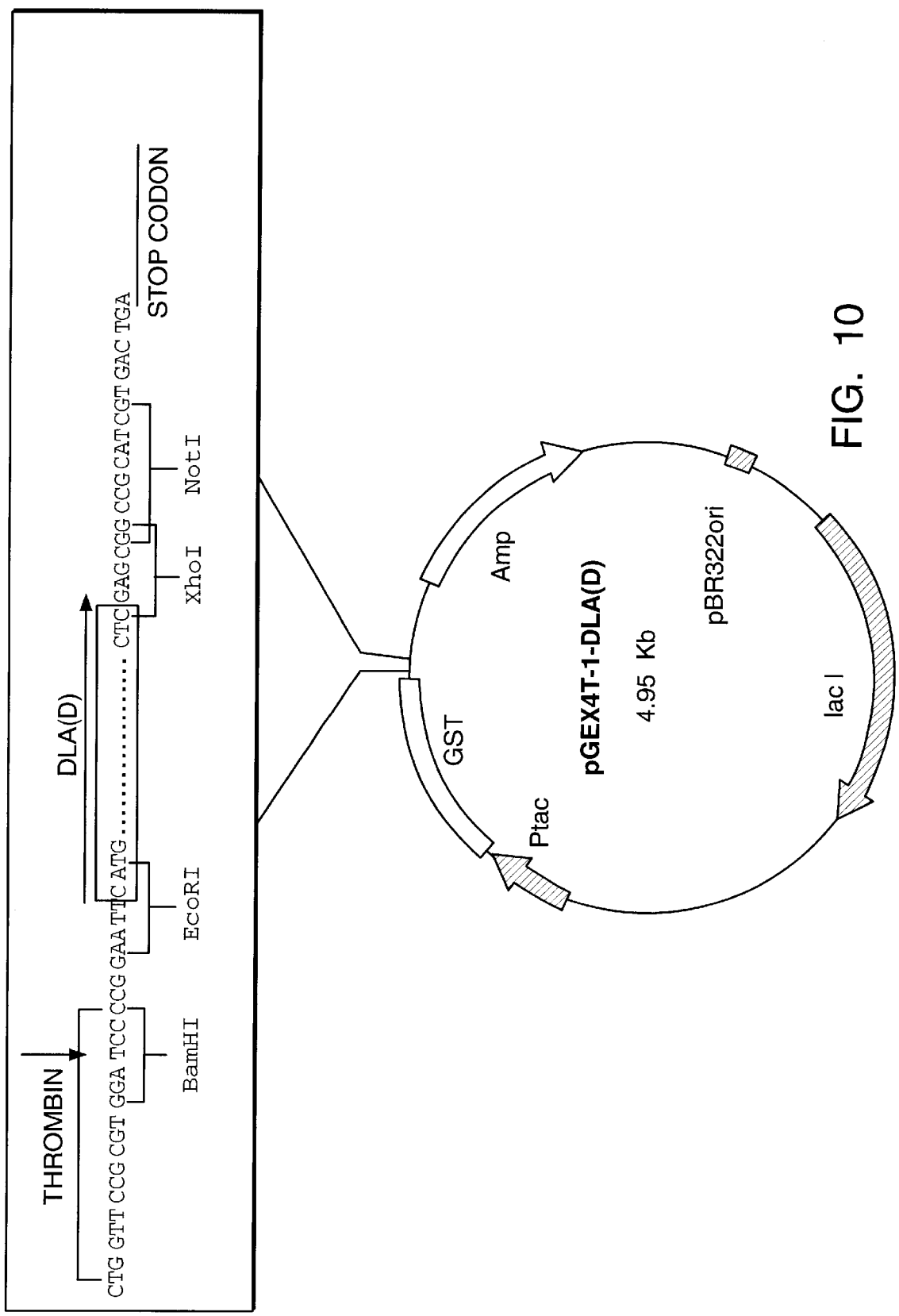
FIG. 10 is a map of a recombinant expression vector pGEX4T-1-DLA(D) manufactured by ligating a mutant cDNA clone in the EcoRI/XhoI site of the E. coli expression vector pGEX4T-1.

The FRIL wild-type cDNA and mutant clones (without signal peptides), were ligated into the EcoRI/SalI and EcoRI/XhoI of the expression vector pGEX 4T-1 (Pharmacia), to form the expression constructs pGEX-M1 and pGEX M1(D), respectively illustrated in FIGS. 9 and 10. The host *E. coli* strain, BL21(D3), was purchased from Novagen, and transformed with the above construct using the calcium chloride method (see Sambrook et al. 1989; Gelvin et al. 1988; Altabella et al. 1990; and Pueyo et al. 1995). The induction of the tac promoter (Ptac) was achieved by adding IPTG (isopropyl-β-D-thiogalactopyranoside) (Sigma) at a 1.0 mM final concentration when the cells reached an optical density of 0.4–0.6 at 600 nm. The cultures were allowed to grow for 12 h at 37° C. after the addition of IPTG. Control non-induced cultures were maintained under similar conditions. The cells were lysed by treatment with 4 mg/mL lysozyme in phosphate-buffered saline containing 1% TRITON® X-100.

Total cellular protein was extracted from transformed *E. coli* cells and analyzed on SDS-PAGE on a 15% gel using a standard procedure (Sambrook et al. 1989). The cells from 1 mL of *E. coli* culture were suspended in the same volume of loading buffer (50 mM Tris HCl pH 6.8, 100 mM DTT, 2% SDS, 10% glycerol, 0.1% bromophenol blue) and vortexed. Following transfer to a nitrocellulose membrane, protein was stained with Coomassie Brilliant Blue R250. A representative separation is shown in FIG. 11, with the lanes identified in Table 1, below.

TABLE 1

Figure 11:
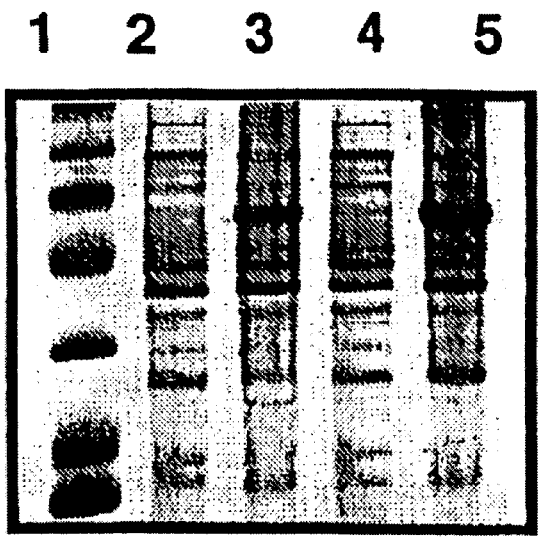
FIG. 11 is an electrophoretogram of a Southern blot of total protein extracts of E. coli cells transformed with the recombinant expression vectors pGEX4T-1-DLA and pGEX4T-1-DLA(D).

Key to FIG. 11

| Lane No. | Content |
|---|---|
| 1 | Molecular Mass Marker (Bio-Rad) |
| 2 | Total Protein Extract from Non-Induced BL21(D3) pGEX-M1 |
| 3 | Total Protein Extract from Induced BL21(D3) pGEX-M1 |
| 4 | Total Protein Extract from Non-Induced BL21(D3) pGEX-M1(D) |
| 5 | Total Protein Extract from Induced BL21(D3) pGEX-M1(D) |

The separation of proteins in FIG. 11 shows that the induced cells ((lanes 3, 5) both produced an abundant polypeptide having a molecular mass of about 60 kDa (indicated by arrow). The non-induced cells failed to produce any significant amount of this protein (lanes 2, 4).

EXAMPLE 8

Purification of Recombinant FRIL

Induced *E. coli* cells (200 mL) as described in Example 7 were harvested after 12 h induction at 37° C. by centrifugation at 5000 g for 10 min. The pellet was washed with 50 mM Tris-HCl pH 8.0, 2 mM EDTA, and resuspended in $\frac{1}{10}$ vol of 1% TRITON surfactant in TBS (20 mM Tris pH 7.5, 500 mM NaCl). The cells were lysed by adding 4 mg/mL of lysozyme and incubating at room temperature for 30–60 min. After centrifugation at 5000 g, the supernatant containing the total soluble proteins was discarded and the resulting pellet, comprising the inclusion bodies and containing the accumulated the recombinant fusion protein, was extracted with 8 M guanidine-HCl (Martson et al. 1993).

The recombinant fusion protein solubilized by guanidine-HCl was purified on GST-Sepharose beads (Pharmacia) according the manufacturer's instructions and eluted in 1 mL of reduced glutathione (Sigma). Samples of the purified fusion proteins were cleaved with thrombin (Novagen) using 5 cleavage units/mL purified fusion protein.

For immunoblot analysis (western blot), the purified proteins were separated by SDS-PAGE in general accordance with the method described in Example 7. The gel was equilibrated in transfer buffer (25 mM Tris pH 8.3, 192 mM Glycine, 20% MeOH) and blotted onto nitrocellulose (Bio-Rad) for 1 h at 100 V using a Bio-Rad electrotransfer apparatus. Non-specific binding was blocked by incubating the blots for at least 1 h in IX TBS (20 mM Tris pH 7.5, 500 mM NaCl) containing 3% gelatin. Blotting was followed by incubation with a primary antibody (a polyclonal rabbit serum raised against the N-terminal peptide of the β-subunit of the *Phaseolus vulgaris* homolog of FRIL, 1:100 dilution, 3 h), followed by incubation with a secondary antibody (goat anti-rabbit IgG conjugated to horseradish peroxidase at 1:1000 dilution for 1 h). The blots were washed and the color developed with the color development reagent (Bio-Rad). A representative result is shown in FIG. 12, with the lanes identified in Table 2, below.

TABLE 2

Figure 12:
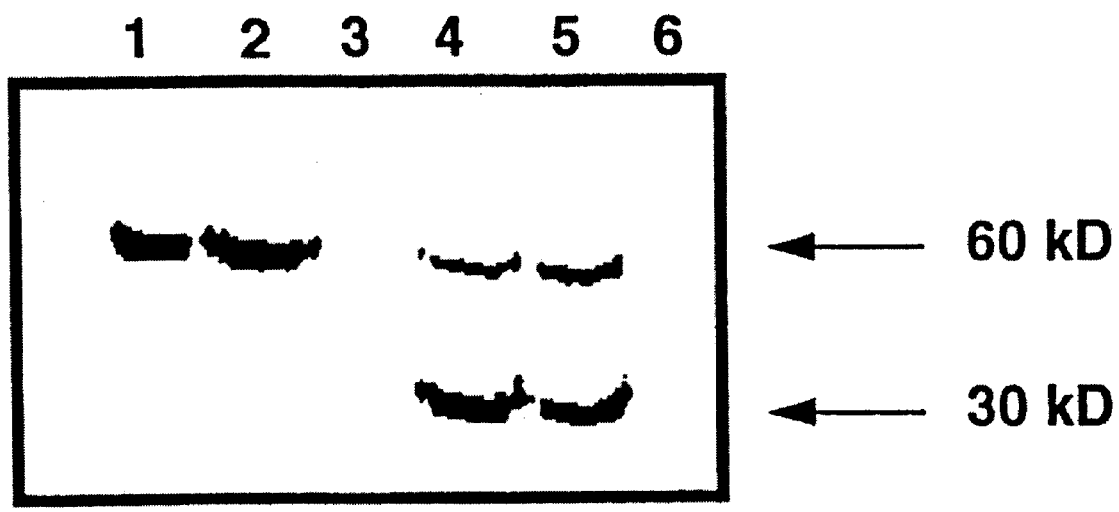
FIG. 12 is an electrophoretogram of a Western blot of purified GST-fusion proteins with and without cleavage by thrombin.

Key to FIG. 12

| Lane No. | Content |
|---|---|
| 1 | Purified Fusion Protein M1 |
| 2 | Purified Fusion Protein M1(D) |
| 3 | Control |
| 4 | Purified Fusion Protein M1 After Cleavage with Thrombin |
| 5 | Purified Fusion Protein M1(D) After Cleavage with Thrombin |
| 6 | Control |

The separation shown in FIG. 12 demonstrates that the two forms of fusion protein have similar molecular masses of about 60 kDa, and that thrombin cleaved both types of fusion protein to produce a new polypeptide of molecular mass 30 kDa.

EXAMPLE 9

Recombinant FRIL Specifically Stimulates Proliferation of 3T3 Cells expressing the FLK2/FLT3 Receptor The recombinant protein interacts with the mammalian FLK2/FLT3 tyrosine kinase receptor. A specific and quantitative biological assay using NIH 3T3 fibroblasts transfected either with a chimeric receptor having the extracellular portion of the murine FLK2/FLT3 receptor combined with the intracellular portion of the human Fms receptor (Dosil et al. 1993) or with the full length human receptor (Small et al. 1994) can be used to evaluate lectin biological activity during purification. Serial two-fold dilutions of lectin samples across rows of a 96 well plate allowed for greater than a thousand-fold range to access FLK2/FLT3 3T3 biological activity. Either the murine or human FLK2/FLT3 ligand (FL) (Lyman et al. 1993; Hannum et al. 1994) or the recombinant protein encoded by the nucleic acid of the invention rescues FLK2/FLT3-transfected cells from death in this assay.

Specifically, 3T3 cells cultured in tissue culture plates (Becton Dickinson Labware, Lincoln Park, N.J.) are removed from the plates by washing cells twice in Hank's buffered saline solution (HBSS; Gibco Laboratories, Grand Island, N.Y.). Non-enzymatic cell dissociation buffer (Gibco) is added for 15 minutes at room temperature. The resulting cells are washed in medium. FLK2/FLT3 3T3 cells are cultured at a final concentration of 3,000 cells per well in a volume of 100 μL of serum-defined medium containing 10 mg/mL rhIL1-α, 10% AIMV (Gibco) and 90% Dulbecco's modification of Eagle's medium (DMEM; Gibco) in 96 well plates. Under these assay conditions, cells die after two to four days of culture in a humidified incubator at 37° C. and 5% $CO_2$ unless exogenously added ligand rescues cells from death. Each 96 well plate contains calf serum, which stimulates all 3T3 cells, as a positive control and medium only as a negative control ("blank"). Full-length Fms-transfected 3T3 cells (biological response shown in Tessler et al. 1994) serve as receptor-transfected control target cells, and parent 3T3 cells serve as untransfected control cells. Proliferation and cell survival is quantitated by addition of XTT (Diagnostic Chemicals Ltd, Charlottetown, Prince Edward Island, Canada), which is a tetraformazan salt cleaved by actively respiring cells (Roehm et al. 1991), quantitated spectrophotometrically using a Vmax kinetic plate reader (Molecular Devices Corp., Mountain View, Calif.), and recorded as either relative activity (units/mL) or as specific activity (units/mg). One unit of biological activity is defined as the reciprocal dilution at which half-maximal stimulation of cells is detected.

The crude protein extract from the E. coli cultures described in Example 7, above, was tested to determine whether expressed recFRIL possessed any capacity to stimulate FLK2/FLT3 3T3 cells using this assay. The data from this experiment are summarized in FIGS. 13A and 13B. Specifically, FIG. 13A is a graph showing that the crude extract of the E. coli culture containing expressed FRIL specifically stimulates hFLK2/FLT3 cells; FIG. 13B is a graph showing that the same extract does not stimulate untransfected 3T3 cells. In FIGS. 13A and 13B, medium control is represented by a solid line. The ordinate (absorbance) indicates cell viability measured by XTT at three days; the abscissa shows the reciprocal dilution of the extract sample. The apparent inhibition of proliferation observed at higher concentrations (FIG. 13A) is not understood, but may relate to toxic components in the crude E. coli extract or the consequences of dose-related preservation of the 3T3 fibroblasts.

EXAMPLE 10

Recombinant FRIL Preserves Mononuclear Cells and Progenitors in Liquid Culture

Figure 14A:
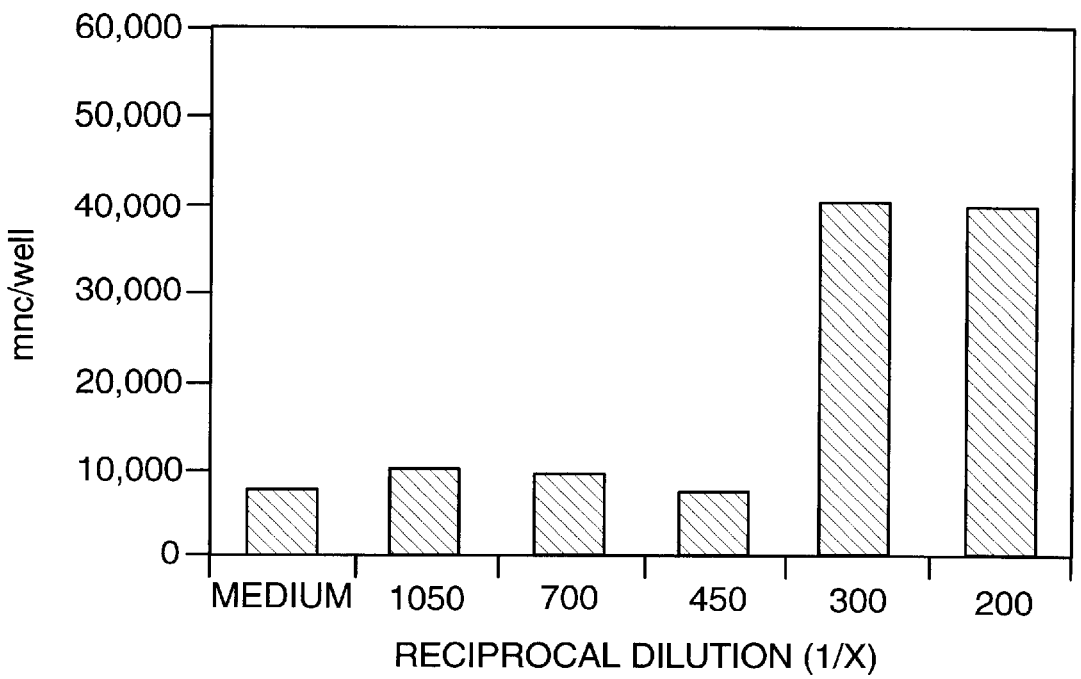
FIG. 14A is a histogram showing that purified recFRIL preserves cord blood mononuclear cells in a dose-responsive manner.
Figure 14B:
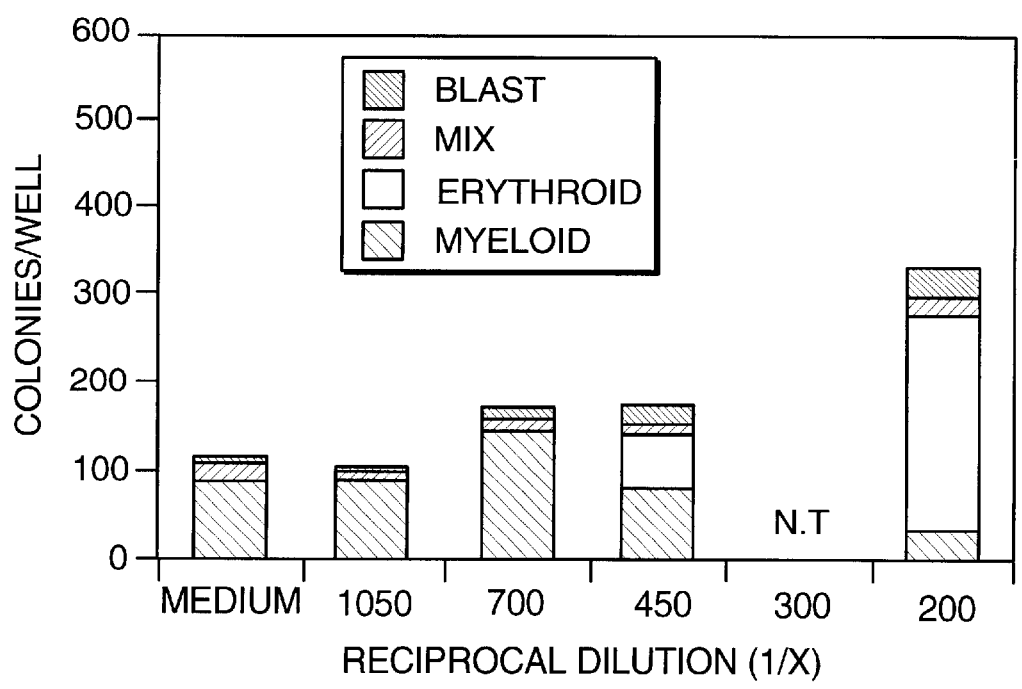
FIG. 14B is a histogram showing that purified recFRIL preserves hematopoietic progenitors in a dose-responsive manner.

The recFRIL protein preserves functional progenitors for at least two weeks in liquid culture. FIGS. 14A and 14B illustrate the results of an experiment in which recFRIL is shown to act in a dose-responsive manner to preserve human cord blood progenitors.

FIGS. 14A and 14B show that recombinant FRIL preserves cord blood mononuclear cells and progenitors in a dose-responsive manner in liquid culture. Cord blood mononuclear cells obtained by FICOLL-PAQUE® separation (Pharmacia Biotech, Piscataway, N.J.) were cultured in serum-free medium (X-VIVO 10, BioWhittaker, Walkersville, Md.) at a concentration of 200,000 cells/mL in a volume of 4 mL for two weeks without medium changes. Harvested cells were pelleted and resuspended in X-VIVO 10 before determining viable cell number by trypan blue (GIBCO, Grand Island, N.Y.) exclusion. These results are shown in FIG. 14A. The progenitor number and capacity of harvested cells were assessed by plating the cells in complete serum-free, methylcellulose colony assay medium (StemCell Technologies, Vancouver, BC, Canada). After two weeks, the resultant colonies were scored and the results are shown in FIG. 14B. In FIGS. 14A and 14B, "blast" refers to colonies consisting of primitive, morphologically undifferentiated cells; "mix" refers to colonies consisting of myeloid and erythroid cells; "erythroid" refers to colonies consisting of erythroid cells; and "myeloid" refers to colonies consisting of myeloid cells. Cell number is shown on the ordinate; the abscissa shows the reciprocal dilution of the sample.

Figure 15:
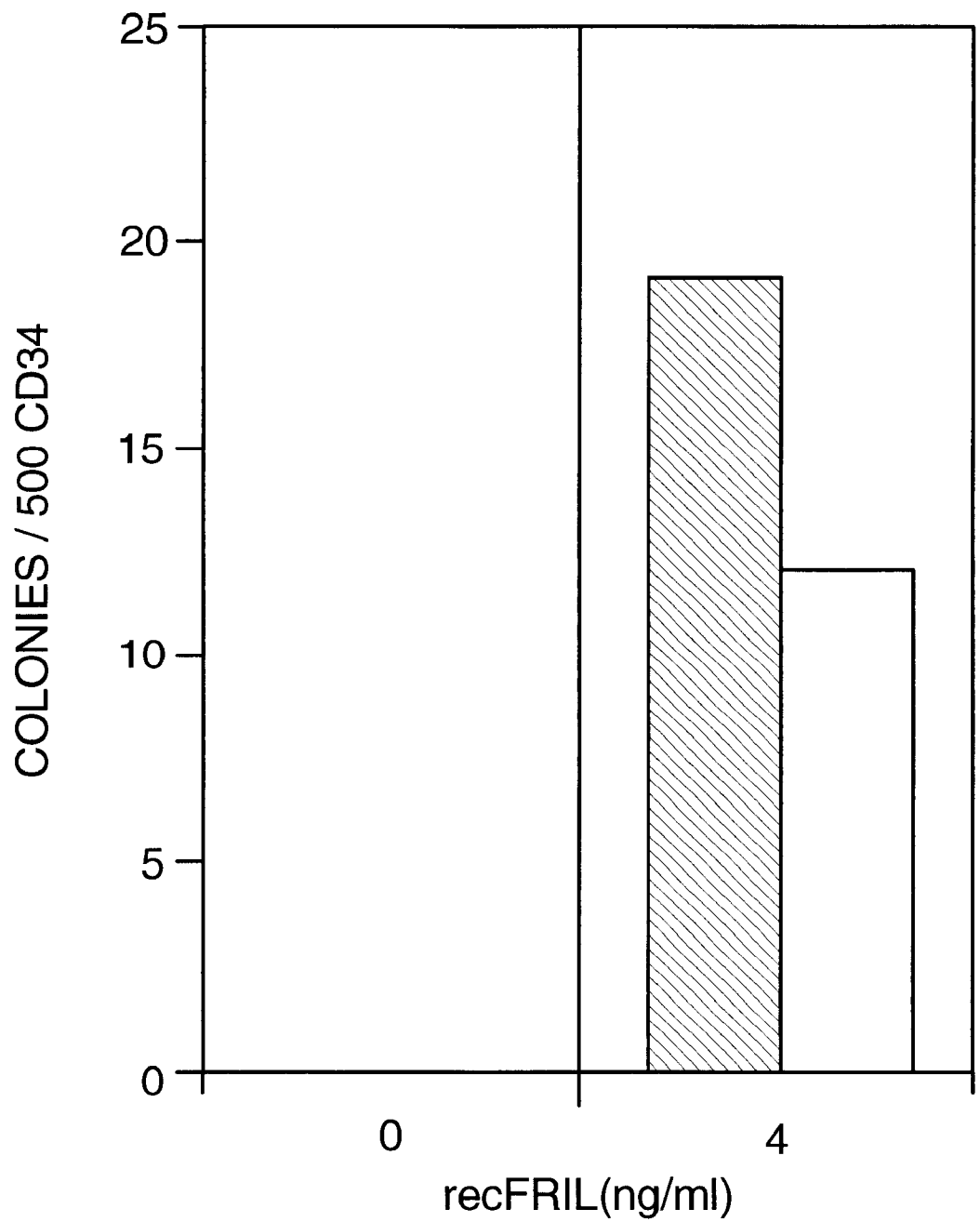
FIG. 15 is a histogram showing that the protein encoded by a nucleic acid of the invention is sufficient to preserve progenitor cells in vitro, whereas a cytokine cocktail fails to preserve such cells.

To assess whether recFRIL acts directly or indirectly through accessory cells to preserve progenitor cells, cord blood mononuclear cells were first enriched for progenitors expressing the CD34 antigen by immunomagnetic bead isolation (Dynal Corp., Lake Success, N.Y.). Five hundred CD34+ cells were placed into wells containing 100 μL of serum-free medium (BIT9500, StemCell Technologies) either in the presence of recFL (PeproTech, Princeton, N.J.) or a cytokine cocktail of rhIL3+rhIL6+rhIL11+rhTpo+FL (BioSource International, Camarillo, Calif.) in 96-well plates and cultured for four weeks without medium changes. The numbers of functional progenitors from these cultures were assessed by plating cells in complete serum-free methylcellulose colony assay medium (StemCell Technologies). After two weeks, the resultant colonies were scored and the results are shown in FIG. 15 (solid bars=recFRIL; open bars=cytokine cocktail). Clearly, progenitors were preserved only in the recFRIL-containing cultures. Thus, purified recFRIL acts directly on primitive hematopoietic progenitors.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following documents have been mentioned in the foregoing specification, and are incorporated herein by reference for all that they disclose:

Abath F G, *Peptide Research* 3(4): 167–168 (1990).

Altabella T, and Chrispeels M J, *Plant Physiol* 93:805–810 (1990).

An G, Ebert P R, Mitra A, and Ha S B, "Binary vectors," in *Plant Molecular Biology Manual*, Vol. A3, Gelvin S B, Schilperoort R A, and Verma D P S, eds., Kluwer Academic Publisher, Dordrecht, The Netherlands, pp. 1–19 (1988).

Baronedes S H, "Bifunctional properties of lectins: Lectins redefined," *Trends Biochem Sci* 13:480–482 (1988).

Berardi A C, Wang A, Levine J D, Lopez P, and Scadden D T, "Functional isolation and characterization of human hematopoietic stem cells," *Science*, 267:104–108 (1995).

Borge et al. (1996).

Caruthers M H, "Gene synthesis machines: DNA chemistry and its uses," *Science* 230(4723):281–285 (1985).

Dallas et al., "The characterization of an *Escherichia coli* plasmid determinant that encodes for the production of a heat-labile enterotoxin," pp. 113–122 in Timmis K N and Puehler A, eds., *Plasmids of Medical, Environmental, and Commercial Importance*, Elsevier/North-Holland Publishing Co., Amsterdam (1975).

Devereux J, Haeberli P, and Smithies O, "A comprehensive set of sequence analysis programs for the VAX," NAR 12:387–394 (1984).

Dieckmann C L and Tzagoloff A, *J Biol Chem* 260(3):1513–1520 (1985).

Dosil M, Wang S, and Lemischka I R, "Mitogenic signalling and substrate specificity of the Flk2/Flt3 receptor tyrosine kinase in fibroblasts and interleukin 3-dependent hematopoietic cells," *Mol Cell Biol* 13(10):6572–6585 (1993).

Dwek R A, "Glycobiology: More function for oligosaccharides," *Science* 269:1234–1235 (1995).

Eaton D, Rodriguez H, and Vehar G A, *Biochemistry* 25(2):505–512 (1986).

Frohman M A, "RACE: Rapid amplification of cDNA ends," pp. 28–38 in *PCR Protocols: A Guide to Methods and Applications*, Innis M A, Gelfand D H, Sninsky J J, and White T J, eds. Academic Press, San Diego (1990).

Gabius H J and Gabius S, eds., *Lectins and Glycobiology*, Springer-Verlag Inc., New York (1 993).

Gabius H-J, "Non-carbohydrate binding partners/domains of animal lectins," *Int J Biochem* 26:469 (1994a).

Gabius H-J, "Lectinology meets mythology: Oncological future for the mistletoe lectin?," *Trends in Glycosci and Glycotech* 6:229 (1994b).

Gelvin S B, and Schilperoort R A, *Plant Molecular Biology Manual*, Kluwer Academic Publishers, Dordrecht, The Netherlands (1988).

Glover D M and Hames B D, eds., *DNA Cloning*, 2d ed., Vols. 1–4, IRL Press, Oxford (1995).

Gowda L R, Savithri H S, and Rao D R, "The complete primary structure of a unique mannose/glucose-specific lectin from field bean (*Dolichos lab lab*)," *J Biol Chem* 269:18789–18793 (1994).

Gray M R, Colot H V, Guarente L, and Rosbash M, "Open reading frame cloning: Identification, cloning and expression of open reading frame DNA," *Proc Natl Acad Sci USA* 79:6598 (1982).

Grunstein M and Hogness D S, "Colony hybridization: A method for the isolation of cloned DNAs that contain a specific gene," *Proc Natl Acad Sci USA* 72(10):3961–3965 (1975).

Guan et al., *Gene* 67:21–30 (1987).

Hames B D and Higgins S J, eds., *Gene Probes I and Gene Probes II*, IRL Press, Oxford (1995).

Higgins T J V, Newbigin E J, Spencer D, Llewellyn D J, and Craig S, "The sequence of a pea vicilin gene and its expression in transgenic tobacco plants," *Plant Mol Biol* 11:683–695 (1988).

Higuchi R, "Recombinant PCR," pp. 177–183 in: *PCR Protocols: A Guide to Methods and Applications*, Innis M A, Gelfand D H, Sninsky J J, and White T J, eds., Academic Press, San Diego (1990).

Hoffman L M, Ma Y, and Barker R F, "Molecular cloning of *Phaseolus vulgaris* lectin mRNA and use of cDNA as a probe to estimate lectin transcripts levels in various tissues," *Nucleic Acids Res* 10:7819–7828 (1982).

Hopp et al., *Biotechnology* 6:1204–1210 (1988).

Horsch R B, Fry J E, Hoffmann N L, Eichholtz D, Rogers S G, and Fraley R T, "A simple and general method for transferring genes into plants," *Science* 227:1229–1231 (1985).

Itakura K, Hirose T, Crea R, Riggs A D, Heyneker H L, Bolivar F, and Boyer H W, *Science* 198(4321):1056–1063 (1977).

Johnson K S, *Nature* 338(6216):585–587 (1989).

Keil B, Giles A M, Lecroisey A, Hurion N, and Tong N T, *FEBS Letters* 56(2):292–296 (1975).

Kaufmann R J and Sharp P A, "Amplification and expression of sequences cotransfected with a modular dihydrofolate reductase complementary DNA gene," *J Mol Biol* 159:601–621 (1982a).

Kaufmann R J and Sharp P A, *Mol Cell Biol* 159:601–664 (1982b).

Keller G H and Manak M M, *DNA Probes*, 2d ed., Macmillan Publishers Ltd., England (1991).

Laemmli U K, "Cleavage of structural proteins during the assembly of the head of bacteriophage T4," *Nature* 227:680–685 (1970).

Leary J J, Brigati D J, and Ward D C, "Rapid and sensitive colorimetric method for visualizing biotin-labeled DNA probes hybridized to DNA or RNA immobilized on nitrocellulose: Bio-blots," *Proc Natl Acad Sci USA* 80:4045 (1983).

Maina C V, Riggs P D, Grandea A G 3d, Slatko B E, Moran L S, Tagliamonte J A, McReynolds L A, and Guan C D, *Gene* 74:36–373 (1988).

Marston, "The purification of eukaryotic proteins expressed in *E. coli*," in *DNA Cloning*, Glover D M, ed., Volume III, IRL Press Ltd., Oxford (1987).

Marston F A O and Hartley D L, "Solubilization of protein aggregates," pp. 266–267 in *Guide to Protein Purification*, Deutscher M P, ed., Academic Press, San Diego (1990).

McPherson M J, ed., *Directed Mutagenesis: A Practical Approach*, IRL Press, Oxford (1991).

Meinkoth J and Wahl G, "Hybridization of nucleic acids immobilized on solid supoports," *Anal. Biochem.* 138(2):267 (1984).

Moreno J and Chrispeels M J, "A lectin gene encodes the α-amylase inhibitor of the common bean," *Proc Natl Acad Sci USA* 86:7885–7889 (1989).

Nagai K and Thogerson H C, *Methods Enzymol* 153:461–481 (1987).

Ogawa M, "Differentiation and proliferation of hematopoietic stem cells," *Blood* 87:2855 (1993).

Pawloski K, Kunze R, de Vries R, and Bisseling T, "Isolation of total, poly(A+) and polysomal RNA from plant tissues," *Mol Plant Biol Manual* 5:1–13 (1994).

Pearson W R and Lipman D J, "Improved tools for biological sequence comparison," *Proc Natl Acad Sci USA* 85:2444–2448 (1988).

Pueyo J J, Chrispeels M J, and Herman E M, *Planta* 196:586–596 (1995).

Pusztai A, and Bardocz S, *Lectins: Biomedical Perspectives*, Taylor & Francis, London (1995).

Renz M and Kurz C, "A calorimetric method for DNA hybridization," *Nucleic Acids Res* 12:3435 (1984).

Richardson and Gumport, *Nucleic Acids Res* 11:6167 (1983).

Riggs P, in Ausebel F M et al., eds., *Current Protocols in Molecular Biology*, Greene Associates/Wiley Interscience, New York (1990).

Roehm N W, Rodgers G H, Hatfield S M, and Glasebrook A L, "An improved colorimetric assay for cell proliferation and viability utilizing the tetrazolium salt XTT," *J Immunol Methods* 142(2):257–265 (1991).

Rotman, *Proc Natl Acad Sci USA* 47:1981–1991 (1961).

Saiki R K, Gelfand D H, Stoffel S, Scharf S J, Higuchi R, Horn G T, Mullis K B, and Erlich H A, *Science* 239:487 (1988).

Sambrook J, Fritsch E F, and Maniatis T, *Molecular Cloning. A Laboratory Manual*, 2d ed., Cold Spring Harbor Laboratory, Cold Spring Harbor (1989).

Scahill S J, Devos R, Van der Heyden J, and Fiers W, "Expression and characterization of the product of a human immune interferon DNA gene in Chinese hamster ovary cells," *Proc Natl Acad Sci USA* 80:4654–4659 (1983).

Shah A J, Smogorzewska E M, Hannum C, and Crooks G M, "Flt3 ligand induces proliferation of quiescent human bone marrow $CD34^+CD38^-$ cells and maintains progenitor cells in vitro," *Blood*, 87:3563–3570 (1996).

Sharon N and Lis H, "Lectins as cell recognition molecules," *Science*, 246:227–234 (1989).

Small D, Levenstein M, Kim E, Carow C, Amim S, Rockwell P, Witte L, Burrow C, Ratajczak M, Gewirtz A M, and Civin C, *Proc Natl Acad Sci USA* 91:459–463 (1994).

Smith L M, Fung S, Hunkapiller M W, Hunkapiller T J, and Hood L E, *Nucleic Acids Res* 13:2399 (1985).

Smith D B, *Gene* 67:31–40 (1988).

Southern P J and Berg P, *J Mol Appl Genet* 1:327–341 (1982).

Subramani S et al., *Mol Cell Biol* 1:854–864 (1981).

Tessler S, Rockwell P, Hicklin D, Cohen T, Levi B-Z, Witte L, Lemischka IR, and Neufeld G, *J Biol Chem*, 269:12456–12461 (1994).

Turhan A G, Humphries R K, Phillips G L, Eaves A C, and Eaves C J, "Clonal hematopoiesis demonstrated by X-linked DNA polymorphisms after allogeneic bone marrow transplantation," *N Engl J Med*, 320:1655–1661 (1989).

Uhlen M, Nilsson B, Guss B, Lindberg M, Gatenbeck S, and Philipson L, *Gene* 23:369–378 (1983).

Ullman, *Gene* 29:27–31 (1984).

Urlaub G and Chasin L A, *Proc Natl Acad Sci USA* 77:4216–4220 (1980).

Van Etten R A, Jackson P, and Baltimore D, *Cell* 58:669–678 (1989).

Young J C, Varma A, DiGiusto D, and Backer M, "Retention of quiescent hematopoietic cells with high proliferative potential during ex vivo stem cell culture," *Blood* 87:545–556 (1996).

Zipori D, "The renewal and differentiation of hemopoietic stem cells," *FASEB J* 6:2691–2697 (1992).

Zoller M J, and Smith M, *Nucleic Acids Res* 10:6487–6500 (1982).

Zoller M J, *Methods Enzymol* 100:468–500 (1983).

Zoller M J, DNA 3(6):479–488 (1984).

What is claimed is:

1. An isolated nucleic acid molecule comprising a sequence that encodes a protein comprising an amino acid sequence as defined by SEQ ID NO:2 or a fragment of the protein, wherein the amino acid sequence of the fragment contains the sequence TNNVLQVT (SEQ ID NO:24).

2. An isolated nucleic acid molecule according to claim 1, comprising a nucleotide sequence as defined by SEQ ID NO:1 or a unique fragment thereof.

3. An isolated nucleic acid molecule that encodes a protein that maintains progenitor cells in a quiescent state, wherein the nucleic acid is isolated from a legume.

4. An isolated nucleic acid molecule according to claim 3, wherein the encoded protein comprises an amino acid sequence as defined by SEQ ID NO:2 or a fragment thereof that contains the sequence TNNVLQVT (SEQ ID NO:24).

5. An isolated nucleic acid molecule according to claim 3, wherein the nucleic acid molecule encodes a mannose/glucose-specific legume lectin.

6. An isolated nucleic acid molecule according to claim 3, wherein the nucleic acid molecule is isolated from a legume from the tribe Phaseoleae.

7. An isolated nucleic acid molecule according to claim 6, wherein the nucleic acid molecule is isolated from red kidney beans, white kidney beans, hyacinth beans, or black-eyed peas.

8. An isolated nucleic acid molecule according to claim 3, wherein the nucleic acid molecule comprises a nucleotide sequence as defined by SEQ ID NO: 1 or a unique fragment thereof.

9. An isolated nucleic acid molecule according to claim 3, wherein the encoded protein maintains progenitor cells that are at least unipotent progenitor cells.

10. An isolated nucleic acid molecule according to claim 3, wherein the encoded protein maintains progenitor cells that are pluripotent progenitor cells.

11. An isolated nucleic acid molecule according to claim 3, wherein the encoded protein maintains progenitor cells that are totipotent progenitor cells.

12. An isolated nucleic acid molecule according to claim 3, wherein the encoded protein maintains progenitor cells that are hematopoietic progenitor cells.

13. An isolated nucleic acid molecule according to claim 3, wherein the encoded protein maintains progenitor cells that comprise blood, nerve, muscle, skin, gut, bone, kidney, liver, pancreas, or thymus progenitor cells.

14. An isolated nucleic acid molecule according to claim 9, wherein the encoded protein maintains progenitor cells that express the CD34 antigen.

15. An isolated nucleic acid molecule according to claim 9, wherein the encoded protein maintains progenitor cells that express the FLK2/FLT3 receptor.

16. An isolated nucleic acid molecule according to claim 15, wherein the encoded protein maintains progenitor cells that are cells modified to express the FLK2/FLT3 receptor on their surface.

17. An isolated nucleic acid molecule according to claim 16, wherein the encoded protein has significant binding affinity for the FLK2/FLT3 receptor on the cells, wherein binding of the encoded protein with the FLK2/FLT3 receptor mediates the inhibition of differentiation of the cells.

* * * * *

UNITED STATES PATENT AND TRADEMARK OFFICE
CERTIFICATE OF CORRECTION

PATENT NO.   : 6,310,195 B1
DATED        : October 30, 2001
INVENTOR(S)  : M. Gabriella Colucci, Maarten J. Chrispeels and Jeffrey G. Moore It is certified that error appears in the above-identified patent and that said Letters Patent is hereby corrected as shown below:

Column 43,
Lines 63-65, should read:

-- 3. An isolated nucleic acid molecule that encodes a protein that maintains progenitor cells in a quiescent state, wherein the nucleic acid molecule is isolated from a legume and wherein the encoded protein comprises the amino acid sequence TNNVLQVT (SED ID NO: 24). --

Column 43, lines 66-67, and column 44, lines 54-55, should read:

-- 4. An isolated nucleic acid molecule according to Claim 3, wherein the encoded protein comprises an amino acid sequence as defined by SED ID NO: 2 or a fragment thereof. --

Signed and Sealed this

Seventh Day of May, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.   : 6,310,195 B1                                              Page 1 of 1
DATED        : March 18, 2003
INVENTOR(S)  : Colucci et al.

It is certified that error appears in the above-identified patent and that said Letters Patent is hereby corrected as shown below:

Column 1,
Line 4, please insert the following paragraph:

-- ACKNOWLEDGEMENT OF GOVERNMENT SUPPORT

This invention was made with Government support under grant DE FG03-86ER13497 awarded by the Department of Energy. The Government has certain rights in this invention. --

Signed and Sealed this

Fifth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,310,195 B1
DATED : October 30, 2001
INVENTOR(S) : Colucci et al.

It is certified that error appears in the above-identified patent and that said Letters Patent is hereby corrected as shown below:

Title page,
Item [73], Assignee, include -- The Regents of the University of California, Oakland, California (US) -- with "ImClone Systems Incorporated, New York, NY (US)".

Signed and Sealed this

Fourteenth Day of December, 2004

JON W. DUDAS
*Director of the United States Patent and Trademark Office*

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 939 nucleotides
       (B) TYPE: nucleic acid
       (C) STRANDEDNESS: double
       (D) TOPOLOGY: linear (xi) SEQUENCE DESCRIPTION: SEQ ID NO:1:

```
GCACAGTCAT TGTCATTTAG TTTCACCAAG TTTGATCCTA ACCAAGAGGA TCTTATCTTC      60

CAAGGTCATG CCACTTCTAC AAACAATGTC TTACAAGTCA CCAAGTTAGA CAGTGCAGGA     120

AACCCTGTGA GTTCTAGTGC GGGAAGAGTG TTATATTCTG CACCATTGCG CCTTTGGGAA     180

GACTCTGCGG TATTGACAAG CTTTGACACC ATTATCAACT TTGAAATCTC AACACCTTAC     240

ACTTCTCGTA TAGCTGATGG CTTGGCCTTC TTCATTGCAC CACCTGACTC TGTCATCAGT     300

TATCATGGTG GTTTTCTTGG ACTCTTTCCC AACGCAAACA CTCTCAACAA CTCTTCCACC     360

TCTGAAAACC AAACCACCAC TAAGGCTGCA TCAAGCAACG TTGTTGCTGT TGAATTTGAC     420

ACCTATCTTA ATCCCGATTA TGGTGATCCA AACTACATAC ACATCGGAAT TGACGTCAAC     480

TCTATTAGAT CCAAGGTAAC TGCTAAGTGG GACTGGCAAA ATGGGAAAAT AGCCACTGCA     540

CACATTAGCT ATAACTCTGT CTCTAAAAGA CTATCTGTTA CTAGTTATTA TGCTGGGAGT     600

AAACCTGCGA CTCTCTCCTA TGATATTGAG TTACATACAG TGCTTCCTGA ATGGGTCAGA     660

GTAGGGTTAT CTGCTTCAAC TGGACAAGAT AAAGAAAGAA ATACCGTTCA CTCATGGTCT     720

TTCACTTCAA GCTTGTGGAC CAATGTGGCG AAGAAGGAGA ATGAAAACAA GTATATTACA     780

AGAGGCGTTC TGTGATGATA TATGTGTATC AATGATTTTC TATGTTATAA GCATGTAATG     840

TGCGATGAGT CAATAATCAC AAGTACAGTG TAGTACTTGT ATGTTGTTTG TGTAAGAGTC     900

AGTTTGCTTT TAATAATAAC AAGTGCAGTT AGTACTTGT                            939
```

(2) INFORMATION FOR SEQ ID NO:2:

(i) SEQUENCE CHARACTERISTICS:
       (A) LENGTH: 270 amino acids
       (B) TYPE: amino acid
       (C) TOPOLOGY: linear (ii) MOLECULE TYPE: peptide (iii) SEQUENCE DESCRIPTION: SEQ ID NO:2:

```
Ala Gln Ser Leu Ser Phe Ser Phe Thr Lys Phe Asp Pro Asn Gln Glu
1               5                   10                  15

Asp Leu Ile Phe Gln Gly His Ala Thr Ser Thr Asn Asn Val Leu Gln
            20                  25                  30

Val Thr Lys Leu Asp Ser Ala Gly Asn Pro Val Ser Ser Ala Gly
        35                  40                  45

Arg Val Leu Tyr Ser Ala Pro Leu Arg Leu Trp Glu Asp Ser Ala Val
        50                  55                  60

Leu Thr Ser Phe Asp Thr Ile Ile Asn Phe Glu Ile Ser Thr Pro Tyr
65                  70                  75                  80

Thr Ser Arg Ile Ala Asp Gly Leu Ala Phe Phe Ile Ala Pro Pro Asp
                85                  90                  95
```

```
Ser Val Ile Ser Tyr His Gly Gly Phe Leu Gly Leu Phe Pro Asn Ala
            100                 105                 110

Asn Thr Leu Asn Asn Ser Ser Thr Ser Glu Asn Gln Thr Thr Thr Lys
        115                 120                 125

Ala Ala Ser Ser Asn Val Val Ala Val Glu Phe Asp Thr Tyr Leu Asn
    130                 135                 140

Pro Asp Tyr Gly Asp Pro Asn Tyr Ile His Ile Gly Ile Asp Val Asn
145                 150                 155                 160

Ser Ile Arg Ser Lys Val Thr Ala Lys Trp Asp Trp Gln Asn Gly Lys
                165                 170                 175

Ile Ala Thr Ala His Ile Ser Tyr Asn Ser Val Ser Lys Arg Leu Ser
            180                 185                 190

Val Thr Ser Tyr Tyr Ala Gly Ser Lys Pro Ala Thr Leu Ser Tyr Asp
            195                 200                 205

Ile Glu Leu His Thr Val Leu Pro Glu Trp Val Arg Val Gly Leu Ser
            210                 215                 220

Ala Ser Thr Gly Gln Asp Lys Glu Arg Asn Thr Val His Ser Trp Ser
225                 230                 235                 240

Phe Thr Ser Ser Leu Trp Thr Asn Val Ala Lys Lys Glu Asn Glu Asn
                245                 250                 255

Lys Tyr Ile Thr Arg Gly Val Leu Tyr Met Cys Ile Asn Asp
                260                 265                 270

(2) INFORMATION FOR SEQ ID NO:3:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO:3:

AARTTYGAYC CWAAYCARGA RGA                                        23

(2) INFORMATION FOR SEQ ID NO:4:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO:4:

TTWCCRTTYT GCCARTCCCA                                            20

(2) INFORMATION FOR SEQ ID NO:5:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO:5:

GTACCGAGCT CGGAT                                                 15

(2) INFORMATION FOR SEQ ID NO:6:

(i) SEQUENCE CHARACTERISTICS:
        (A) LENGTH: 18 nucleotides
        (B) TYPE: nucleic acid
```

(C) STRANDEDNESS: single
        (D) TOPOLOGY: linear (xi) SEQUENCE DESCRIPTION: SEQ ID NO:6:

TCTAGATGCA TGCTCGAG                                                         18

(2) INFORMATION FOR SEQ ID NO:7:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO:7:

GTTGGACGTC AATTCCGATG TG                                                    22

(2) INFORMATION FOR SEQ ID NO:8:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO:8:

GCYCARTCYC TYTCYTT                                                          17

(2) INFORMATION FOR SEQ ID NO:9:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO:9:

GACCACGCGT ATCGATGTCG AC                                                    22

(2) INFORMATION FOR SEQ ID NO:10:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO:10:

AAGTTAGACA GTGCAGGAAA C                                                     21

(2) INFORMATION FOR SEQ ID NO:11:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO:11:

GCACAGTCAT TGTCATTTAG                                                       20

(2) INFORMATION FOR SEQ ID NO:12:

(i) SEQUENCE CHARACTERISTICS:
        (A) LENGTH: 132 amino acids
        (B) TYPE: amino acid
        (C) TOPOLOGY: linear (ii) MOLECULE TYPE: peptide (iii) SEQUENCE DESCRIPTION: SEQ ID NO:12:

Ile Ala Glu Ser Asn Val Val Ala Val Glu Phe Asp Thr Asp Tyr Leu
1               5                   10                  15

Asn Pro Asp Tyr Gly Asp Pro Asn Tyr Ile His Ile Gly Ile Asp Val
            20                  25                  30

Asn Ser Ile Arg Ser Lys Val Thr Ala Ser Trp Asp Trp Gln Asn Gly
            35                  40                  45

Lys Ile Ala Thr Ala His Ile Ser Tyr Asn Ser Val Ser Lys Arg Leu
    50                  55                  60

Ser Val Thr Thr Tyr Tyr Pro Gly Arg Gly Lys Pro Ala Thr Ser Tyr
65                  70                  75                  80

Asp Ile Glu Leu His Thr Val Leu Pro Glu Trp Val Arg Val Gly Leu
                85                  90                  95

Ser Ala Ser Thr Gly Gln Asn Ile Glu Arg Asn Thr Val His Ser Trp
                100                 105                 110

Ser Phe Thr Ser Ser Leu Trp Thr Asn Val Ala Lys Val Gly Val Ala
            115                 120                 125

Ser Ile Ser Gly
            130

(2) INFORMATION FOR SEQ ID NO:13:

(i) SEQUENCE CHARACTERISTICS:
        (A) LENGTH: 105 amino acids
        (B) TYPE: amino acid
        (C) TOPOLOGY: linear (ii) MOLECULE TYPE: peptide (iii) SEQUENCE DESCRIPTION: SEQ ID NO:13:

Ala Gln Ser Leu Ser Phe Ser Phe Thr Lys Phe Asp Pro Asn Gln Glu
                5                   10                  15

Asp Leu Ile Phe Gln Gly Thr Ala Thr Ser Lys Leu Asp Ser Ala Gly
            20                  25                  30

Asn Pro Val Ser Ser Ser Ala Gly Arg Val Leu Tyr Ser Ala Pro Leu
            35                  40                  45

Arg Leu Trp Glu Asp Ser Ala Val Leu Thr Ser Phe Asp Pro Thr Ile
    50                  55                  60

Tyr Ile Phe Thr Asn Tyr Thr Ser Arg Ile Ala Asp Gly Leu Ala Phe
65                  70                  75                  80

Ile Ala Pro Pro Asp Ser Val Ile Ser Tyr His Gly Gly Phe Leu Gly
                85                  90                  95

Leu Phe Pro Asn Ala Ala Glu Ser Gly
            100                 105

(2) INFORMATION FOR SEQ ID NO:14:

(i) SEQUENCE CHARACTERISTICS:
        (A) LENGTH: 18 amino acids
        (B) TYPE: amino acid
        (C) TOPOLOGY: linear (ii) MOLECULE TYPE: peptide (iii) SEQUENCE DESCRIPTION: SEQ ID NO:14:

Tyr Leu Asn Pro Asp Tyr Gly Asp Pro Asn Tyr Ile His Ile Gly Ile
                5                   10                  15

Asp Val (2) INFORMATION FOR SEQ ID NO:15:

(i) SEQUENCE CHARACTERISTICS:
        (A) LENGTH: 19 amino acids
        (B) TYPE: amino acid
        (C) TOPOLOGY: linear (ii) MOLECULE TYPE: peptide (iii) SEQUENCE DESCRIPTION: SEQ ID NO:15:

Phe Tyr Asn Ala Ala Trp Asp Pro Ser Asn Arg Asp Arg His Ile Gly
               5                       10                 15

Ile Asp Val (2) INFORMATION FOR SEQ ID NO:16:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO:16:

CCATAATCGG GATCAAGATA GGTG                                         24

(2) INFORMATION FOR SEQ ID NO:17:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO:17:

CACCTATCTT GATCCCGATT ATGG                                         24

(2) INFORMATION FOR SEQ ID NO:18:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO:18:

AACTCAGCCG CACAGTCATT GTCA                                         24

(2) INFORMATION FOR SEQ ID NO:19:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (xi) SEQUENCE DESCRIPTION: SEQ ID NO:19:

GAATTCGACC ACGCGTATCG ATGTCGAC                                   28

(2) INFORMATION FOR SEQ ID NO:20:

(i) SEQUENCE CHARACTERISTICS:
        (A) LENGTH: 21 nucleotides
        (B) TYPE: nucleic acid
        (C) STRANDEDNESS: single (D) TOPOLOGY: linear (xi) SEQUENCE DESCRIPTION: SEQ ID NO:20:

GAATTCATGG CTTCCTCCAA C                                              21

(2) INFORMATION FOR SEQ ID NO:21:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (xi) SEQUENCE DESCRIPTION: SEQ ID NO:21:

TGACTGTGCG GCTGAGTTTG CGTGGGTG                                       28

(2) INFORMATION FOR SEQ ID NO:22:

(i) SEQUENCE CHARACTERISTICS:
        (A) LENGTH: 1005 nucleotides
        (B) TYPE: nucleic acid
        (C) STRANDEDNESS: double
        (D) TOPOLOGY: linear (xi) SEQUENCE DESCRIPTION: SEQ ID NO:22:

ATGGCTTCCT CCAACTTACT CACCCTAGCC CTCTTCCTTG TGCTTCTCAC CCACGCAAAC      60

TCAGCCGCAC AGTCATTGTC ATTTAGTTTC ACCAAGTTTG ATCCTAACCA AGAGGATCTT     120

ATCTTCCAAG GTCATGCCAC TTCTACAAAC AATGTCTTAC AAGTCACCAA GTTAGACAGT     180

GCAGGAAACC CTGTGAGTTC TAGTGCGGGA AGAGTGTTAT ATTCTGCACC ATTGCGCCTT     240

TGGGAAGACT CTGCGGTATT GACAAGCTTT GACACCATTA TCAACTTTGA AATCTCAACA     300

CCTTACACTT CTCGTATAGC TGATGGCTTG GCCTTCTTCA TTGCACCACC TGACTCTGTC     360

ATCAGTTATC ATGGTGGTTT TCTTGGACTC TTTCCCAACG CAAACACTCT CAACAACTCT     420

TCCACCTCTG AAAACCAAAC CACCACTAAG GCTGCATCAA GCAACGTTGT TGCTGTTGAA     480

TTTGACACCT ATCTTAATCC CGATTATGGT GATCCAAACT ACATACACAT CGGAATTGAC     540

GTCAACTCTA TTAGATCCAA GGTAACTGCT AAGTGGGACT GGCAAAATGG GAAAATAGCC     600

ACTGCACACA TTAGCTATAA CTCTGTCTCT AAAAGACTAT CTGTTACTAG TTATTATGCT     660

GGGAGTAAAC CTGCGACTCT CTCCTATGAT ATTGAGTTAC ATACAGTGCT TCCTGAATGG     720

GTCAGAGTAG GGTTATCTGC TTCAACTGGA CAAGATAAAA AAAGAAATAC CGTTCACTCA     780

TGGTCTTTCA CTTCAAGCTT GTGGACCAAT GTGGCGAAGA AGGAGAATGA AAACAAGTAT     840

ATTACAAGAG GCGTTCTGTG ATGATATATG TGTATCAATG ATTTTCTATG TTATAAGCAT     900

GTAATGTGCG ATGAGTCAAT AATCACAAGT ACAGTGTAGT ACTTGTATGT TGTTTGTGTA     960

AGAGTCAGTT TGCTTTTAAT AATAACAAGT GCAGTTAGTA CTTGT                    1005

(2) INFORMATION FOR SEQ ID NO:23:

(i) SEQUENCE CHARACTERISTICS:
        (A) LENGTH: 286 amino acids
        (B) TYPE: amino acid
        (C) TOPOLOGY: linear (xi) SEQUENCE DESCRIPTION: SEQ ID NO:23:

Met Ala Ser Ser Asn Leu Leu Thr Leu Ala Leu Phe Leu Val Leu Leu
                 5                  10                  15

Thr His Ala Asn Ser Ala Ala Gln Ser Leu Ser Phe Ser Phe Thr Lys
             20                  25                  30

```
Phe Asp Pro Asn Gln Glu Asp Leu Ile Phe Gln Gly His Ala Thr Ser
         35                  40                  45
Thr Asn Asn Val Leu Gln Val Thr Lys Leu Asp Ser Ala Gly Asn Pro
         50                  55                  60
Val Ser Ser Ser Ala Gly Arg Val Leu Tyr Ser Ala Pro Leu Arg Leu
65                   70                  75                  80
Trp Glu Asp Ser Ala Val Leu Thr Ser Phe Asp Thr Ile Ile Asn Phe
                 85                  90                  95
Glu Ile Ser Thr Pro Tyr Thr Ser Arg Ile Ala Asp Gly Leu Ala Phe
             100                 105                 110
Phe Ile Ala Pro Pro Asp Ser Val Ile Ser Tyr His Gly Gly Phe Leu
             115                 120                 125
Gly Leu Phe Pro Asn Ala Asn Thr Leu Asn Asn Ser Ser Thr Ser Glu
        130                 135                 140
Asn Gln Thr Thr Thr Lys Ala Ala Ser Ser Asn Val Val Ala Val Glu
145                 150                 155                 160
Phe Asp Thr Tyr Leu Asn Pro Asp Tyr Gly Asp Pro Asn Tyr Ile His
             165                 170                 175
Ile Gly Ile Asp Val Asn Ser Ile Arg Ser Lys Val Thr Ala Lys Trp
             180                 185                 190
Asp Trp Gln Asn Gly Lys Ile Ala Thr Ala His Ile Ser Tyr Asn Ser
         195                 200                 205
Val Ser Lys Arg Leu Ser Val Thr Ser Tyr Tyr Ala Gly Ser Lys Pro
         210                 215                 220
Ala Thr Leu Ser Tyr Asp Ile Glu Leu His Thr Val Leu Pro Glu Trp
225                 230                 235                 240
Val Arg Val Gly Leu Ser Ala Ser Thr Gly Gln Asp Lys Glu Arg Asn
                 245                 250                 255
Thr Val His Ser Trp Ser Phe Thr Ser Ser Leu Trp Thr Asn Val Ala
             260                 265                 270
Lys Lys Glu Asn Glu Asn Lys Tyr Ile Thr Arg Gly Val Leu
             275                 280                 285

(2) INFORMATION FOR SEQ ID NO: 24:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 24:

Thr Asn Asn Val Leu Gln Val Thr
```